(12) United States Patent
Harburger et al.

(10) Patent No.: US 11,654,165 B2
(45) Date of Patent: May 23, 2023

(54) AIRWAY MEDICAMENTS

(71) Applicant: Trench Therapeutics, Inc., Portola Valley, CA (US)

(72) Inventors: David S. Harburger, Carlisle, MA (US); Prashant Girinath, Arlington, MA (US)

(73) Assignee: Trench Therapeutics, Inc., Portola Valley, CA (US)

( * ) Notice: Subject to any disclaimer, the term of this patent is extended or adjusted under 35 U.S.C. 154(b) by 0 days.

(21) Appl. No.: 17/524,923

(22) Filed: Nov. 12, 2021

(65) Prior Publication Data
US 2022/0072072 A1     Mar. 10, 2022

Related U.S. Application Data

(63) Continuation of application No. PCT/US2021/034464, filed on May 27, 2021.

(60) Provisional application No. 62/704,770, filed on May 28, 2020.

(51) Int. Cl.
| | | |
|---|---|---|
| A61K 35/741 | (2015.01) | |
| A61K 35/00 | (2006.01) | |
| A61M 15/00 | (2006.01) | |
| A61M 15/08 | (2006.01) | |
| A61K 35/747 | (2015.01) | |

(52) U.S. Cl.
CPC .......... *A61K 35/747* (2013.01); *A61K 35/741* (2013.01); *A61K 2035/115* (2013.01); *A61M 15/009* (2013.01); *A61M 15/08* (2013.01)

(58) Field of Classification Search
CPC ............ A61K 35/741; A61K 2035/115; A61K 35/74; A61M 15/009; A61M 15/08; A61P 11/02
See application file for complete search history.

(56) References Cited

U.S. PATENT DOCUMENTS

| | | | |
|---|---|---|---|
| 11,406,671 B2 * | 8/2022 | Liu ................ | A61K 9/0043 |
| 2007/0031512 A1 | 2/2007 | Hughes | |
| 2007/0280949 A1 | 12/2007 | Alfa | |
| 2009/0005339 A1 | 1/2009 | Scholz | |
| 2016/0051599 A1 | 2/2016 | Drahos et al. | |
| 2017/0151291 A1 | 6/2017 | Henn et al. | |
| 2018/0185420 A1 | 7/2018 | Liu et al. | |
| 2019/0054128 A1 | 2/2019 | Lebeer | |
| 2019/0167734 A1 | 6/2019 | Gaillard et al. | |
| 2019/0216862 A1 | 7/2019 | Goodman et al. | |
| 2020/0061130 A1 | 2/2020 | Borody | |
| 2020/0297605 A1 | 9/2020 | Ambrogio | |
| 2022/0143104 A1 * | 5/2022 | Lebeer .................. | A61P 11/06 |
| 2022/0202879 A1 | 6/2022 | Zhou | |

FOREIGN PATENT DOCUMENTS

| | | |
|---|---|---|
| EP | 3601525 A1 | 2/2020 |
| EP | 4082545 A1 | 11/2022 |
| WO | 2016172686 A1 | 10/2016 |
| WO | 2019023555 A1 | 1/2019 |
| WO | 2019241339 A1 | 12/2019 |
| WO | 2020117359 A1 | 6/2020 |
| WO | 2020128022 A1 | 6/2020 |
| WO | 2023279093 A1 | 1/2023 |
| WO | 2023281284 A1 | 1/2023 |

OTHER PUBLICATIONS

Bergey's Manual of Systematic Bacteriology vol. 3: The Firmicutes (Vos, G. Garrity, D. Jones, N. R. Krieg, W. Ludwig, F. A. Rainey, K.-H. Schleifer, & W. B. Whitman, Eds.; 2nd ed. 2009.). Springer New York. https://doi.org/10.1007/978-0-387-68489-5, pp. 572 and 573 Only.*

Abbas et al., "IgY antibodies for the immunoprophylaxis and therapy of respiratory infections," Human Vaccines & immunotherapeutics (2019); 15(1):264-275.

Bell et al., "Invited Review: From nose to gut—the role of the microbiome in neurological disease," Neuropathology and Applied Neurobiology (Oct. 8, 2018); 45(3):195-215 Abstract Only.

Bielen et al., "Animal models of hospital-acquired pneumonia: current practices and future perspectives," Ann Transl Med (2017); 5(6):13 pages.

Biesbroek et al., "The Impact of Breastfeeding on Nasopharyngeal Microbial Communities in Infants," American Journal of Respiratory and Critical Care Medicine (Aug. 1, 2014); 190(3):298-308.

Binks et al., "Molecular surveillance of true nontypeable Haemophilus influenzae: an evaluation of PCR screening assays," PloS one (2012); 7(3):e34083.

Bowers et al., "Assessment of the Nasopharyngeal Bacterial Flora of Rhesus Macaques: *Moraxella, Neisseria, Haemophilus*, and other Genera," Journal of Clinical Microbiology (Nov. 2002); 40(11):4340-4342.

Brugger et al., "Dolosigranulum pigrum cooperation and competition in human nasal microbiota," Msphere (2020); 5(5):e00852-20 (76 pages).

Carvalho De Sa Fialho et al., "Role of probiotics Bifidobacterium breve and Lactobacillus rhamnosus on inflammation lung in an experimental model of chronic obstructive pulonary disease," The FASEB Journal (Apr. 1, 2019); 33(1):3 pages.

Chertow et al., "Influenza A and methicillin-resistant *Staphylococcus aureus* co-infection in rhesus macaques—A model of sever pneumonia," Antiviral Research (2016); 129:120-129.

Coffey MJ et al., "Probiotics for people with cystic fibrosis (Protocol)," Cochrane Database of Systematic Reviews (2018); Issue 2, Article No. CD012949.

(Continued)

*Primary Examiner* — Kade Ariani
(74) *Attorney, Agent, or Firm* — Greenberg Traurig, LLP

(57) ABSTRACT

Described herein are compositions, methods, kits and devices for the treatment and/or prevention of a wide spectrum of disease conditions. In particular, bacterial populations described herein are live, purified bacteria for the modulation, restoration and/or promotion of the microbiome in the upper respiratory tract of a subject, including the nasal cavity, to promote health. Such bacterial populations may include single or multiple strains for bacteria. The multiple strains of bacteria may be strains from the same or different species, including species of *Corynebacterium* and/or *Dolosigranulum pigrum*.

9 Claims, 6 Drawing Sheets

(56) References Cited

OTHER PUBLICATIONS

Cortese et al., "Preliminary Evidence for differential olfactory and trigeminal processing in combat veterans with and without PTSD," NeuroImage: Clinical (2018); 17:378-387.
Dando et al., "Pathogens Penetrating the Central Nervous System: Infection Pathways and the Cellular and Molecular Mechanisms of Invasion," Clinical Microbiology Reviews (Oct. 2014); 27(4):691-726.
DeBoeck et al., "Lactobacilli Have a Niche in the Human Nose," Cell Reports (2020); 31:107674 (21 pages).
Durack et al., "Human Respiratory and Gut Microbiomes—Do They Really Contribute to Respiratory Health?," Froniters in Pediatrics (Sep. 2020); 8:Article 528 (12 pages).
Geramita et al., "Decreased Amplitude and reliability of odor-evoked responses in two mouse models of autism," J Neurophysiol (2020); 123:1283-1294.
Gong et al., "The gut microbiome and response to immune checkpoint inhibitors: preclinical and clinical strategies," Clin Trans Med (2019); 8:9 (14 pages).
Luis Gosalbez, "The Microbiome Biotech Landscape: An Analysis of the Pharmaceutical Pipeline," Microbiome Times Magazine (Mar. 26, 2020); download from https://www.microbiometimes.com/the-microbiome-biotech-landscape-an-analysis-of-the-pharmaceutical-pipeline/ (13 pages).
Gray et al., "A Novel Translational Ovine Pulonary Adenocarcinoma Model for Human Lung Cancer," Frontiers in Oncology (Jun. 19, 2019); 9:Article 534 (17 pages).
Harata et al., "Intranasal admniistration of Lactobacillus rhamnosus G protects mice from H1N1 influenza virus infection by regulating respiratory immune responses," Letters in Applied Microbiology (2010); 50:597-602.
Hardy et al., "Corynebacterium pseudodiphtheriticum Exploits *Staphylococcus aureus* Virulence Components in a Novel Polymicrobial Defense Strategy," mBio (Jan./Feb. 2019); 10(1); e02491-18 (24 pages).
Hardy et al., "Antimicrobial Activity of Clinically Isolated Bacterial Species Against *Staphylococcus aureus*," Frontiers in Microbiology (Jan. 15, 2020); 10:Article 2977 (15 pages).
Higgins et al., "Intranasal Antiviral Drug Delivery and Coronavirus Disease 2019 (COVID-19): A State of the Art Review," Otolaryngology—Head and Neck Surgery (2020); 163(4):682-694.
Hou et al., "Sars-CoV-2 Revers Genetics Reveals a Variable Infection Gradient in the Respiratory Tract," Cell (2020); 182:429-446.
Howell et al., "Head trauma and olfactory function," World Journal of Otorhinolaryngology—Head and Neck Surgery (2018); 4:39-45.
Iravani et al., "Pramipexole protects against MPTP toxicity in non-human primates," Journal of Neurochemistry (2006); 96:1315-1321.
Islam et al., "Dolosigranulum pigrum modulates immunity against SARS-CoV-2 in respiratory epithelial cells," Pathogens (2021); 10(6): 634.
Jang et al,, "Asthma Prevention by Lactobacillus Rhamnosus in a Mouse Model is Associated with CD4+CD25+Foxp3+ T Cells," Allergy Asthma Immunol Res. (May 2012); 4(3):150-156.
Kanmani et al., "Respiratory Commensal Bacteria Corynebacterium pseudodiphtheriticum Improves Resistance of Infant Mice to Respiratory Syncytial Virus and *Streptococcus pneumoiae* Superinfection," Frontiers in Microbiolgy (Aug. 2017); 8:Article 1613 (14 pages).
Karlyshev et al, "Draft Genome Sequence of Corynebacterium pseudodiphtheriticum Strain 090104 "Sokolov"," Genome Annoucements (Nov./Dec. 2013); 1(6):e00921-13 (2 pages).

Khailova et al., "Lactobacillus Rhamnosus GG Improves Outcome in Experimental Pseudomonas Aeruginosa Pneumonia: Potential Role of Regulatory T Cells," Shock (Dec. 2013); 40(6):496-503.
Kiryukhina et al., "Use of Corynebacterium pseudodiphtheriticum for elimination of *Staphylococcus aureus* from the nasal cavity in volunteers exposed to abnormal microclimate and altered gaseous environment," Probiotics and Antimicrobial Proteins (2013); 5(3)—9 pages.
Koskinen et al., "The nasal microbiome mirrors and potentially shapes olfactory function," Scientific Reports (2018); 8:1296—11 pages.
Kumpitsch et al., "The microbiome of the upper respiratory tract in health and disease," BMC Biology (2019) 17:87—20 pages.
LaClaire et al., "Antimicrobial Susceptibility and Clinical Sources of Dolosigranulum pigrum Cultures," Antimicrobial Agents and Chemotherapy (Jul. 2000); 44(7):2001 2003.
Lappan et al., "Corynebacterium and Dolosigranulum: future probiotic candidates for upper respiratory tract infections," Microbiology Australia (Nov. 2019); 10:1071/MA19052; pp. 172-177.
Le Noci et al., "Modulation of Pulmonary Microbiota by Antibiotic or Probiotic Aerosol Therapy: A Strategy to Promote Immunosurveillance against Lung Metastases," Cell (2018); 24:3528-3538.
Liu et al., "*Staphylococcus aureus* and the ecology of the nasal microbiome," Sci. Adv. (2015); 1:e1400216 (7 pages).
Man et al,"The microbiota of the respiratory tract: gatekeeper to respiratory health," Microbiology (May 2017); 15:259-270.
Martinez-Olondris, "An experimental model of pneumonia induced by methicillin-resistant *Staphylococus aureus* in ventilated piglets," Eur Respir J (2010); 36:901-906.
Moodley et al., "Current Status and Initial Considerations for Successful Development and Commercialization of Microbiome Therapies," Syneos Health (Apr. 2019); 9 pages.
Moyano et al., "The Ability of Respiratory Commensal Bacteria to Beneficially Modulate the Lung Innate Immune Response Is a Strain Dependent Characteristic," Microorganisms (2020); 8:727 (23 pages).
Imke Mulder, "Live Biotherapeutics to Target the Gut-Brain Axis," 3rd Microbiome Movement (Dec. 3-5, 2019), Boston, MA.
O'Dwyer et al, "Lung Microbiota Contribute to Pulmonary Inflammation and Disease Progression in Pulmonary Fibrosis," American Journal of Respiratory and Critical Care Medicine (May 1, 2019); 199(9):1127-1138.
Park et al., "Instranasal Application of S. epidermidis Prevents Colonizationby Methicillin-Resistant *Staphylococcus aureus* in Mice," PLoSONE (Oct. 2011); 6(10):e25880 (5 pages).
Pauly et al., "IgY Technology: Extraction of Chicken Antibodies from Egg Yolk by Polyethylene Glycol (PEG) Precipitation," Journal of Visualized Experiments (May 2011); 51:e3084 (6 pages).
Pellaton et al., "Intragastric and intranasal Administration of Lactobacillus paracasei NCC2461 Moduclates Allergic Airway Inflammation in Mice," International Journal of Inflammation (Mar. 1, 2012); 2012:686739 (8 pages).
Ramsey et al., "*Staphylococcus aureus* Shifts toward Commensalism in Response to *Corynebacterium* Species," Frontiers in Microbiology (Aug. 17, 2016); 7:Article 1230 (15 pages).
Rawls et al., "The microbiome of the nose," Ann Allergy Asthma Immunol (2019); 122:17-24.
Rey et al., "The olfactory bulb as the entry site for prion-like propagation in neurodegenerative diseases," Neurobiology of Disease, (2018) 109:226-248.
Rockx et al., "Comparative pathogensis of COVID-19, MERS, and SARS in a nonhuman primate model," Science (2020); 368:1012-1015.
Kelley Servick, Do gut bacteria make a second home in our brains? Science (Nov. 9, 2018); doi: 10.1126/science.aaw0147 (6 pages).
Spacova et al., "intranasal administration of probiotic Lactobacillus rhamnosus GG prevents birch pollen-induced allergic asthma in a murine model," Allergy (Jun. 10, 2018); 74(1):100-110.
Sungnak et al., SARS-CoV-2 entry factors are highly expressed in nasal epithelial cells togther with innate immune genes, Nature Medicine (May 2020); 26:681-687.

(56) References Cited

OTHER PUBLICATIONS

Tan et al., "Moraxella catarrhalis phase-variable loci show differences in expression during conditions relevant to disease," PLoS ONE (2020); 15(6):e0234306 (18 pages).
Tang et al., "Intranasal Delivery of Bone Marrow Stromal Cells Preconditioned with Fasudil to Treat a Mouse Model of Parkinson's Disease," Neuropsychiatric Disease and Treatment (2020); 16:249-262.
Thoracic Key, From Cancer Mimicking Orphan Lung Disease to orphan Thoracic Oncology—downloaded on Nov. 29, 2021 from https://thoracickey.com/com-cancer-mimicking-orphan-lung-disease-to-orphan-thoracic-oncology/.
Tian et al., "Effects of probiotics on chemotherapy in patients with lung cancer," Oncology Letters (2019); 17:2836-2848.
Tong et al., "Alterations to the Lung Microbiome in Idiopathic Pulmonary Fibrosis Patients," Frontiers in Cellular and Infection Microbiology (May 2019); 9:Article149 (11 pages).
Tsukamoto et al., "Antibodies against swine influenza virus neutralize the pandemic influenza virus A/H1N1," Molecular Medicine Reports (2011); 4:209-214.
Venezia et al., "Characterization of *Corynebacterium* species in macaques," Journal of Medical Microbiology (2012); 61:1401-1408.
Walkden et al., "Injury to the nose increases risk of bacteria entering the brain," Neuroscience News (downloaded Nov. 29, 2021 from https://nerosciencenews.com/nose-brain-bacteria-15930/.
Wolfe et al., "Co-occurence of SARS-CoV-2 and Respiratory Pathogens in the Frail Elderly," doi:https://doi.org/10.1101/2020.06.24.20138941.
Wooster et al., "Polymorphisms in the ACE2 Locus Associate with Severity of COVID-19 Infection," doi:https://doi.org/10.1101/2020.06.18.20135152.
Yadav et al., In Vitro *Streptococcus pneumoniae* Biofilm Formation and In Vivo Middle Ear Mucosal Biofilm in a Rat Model of Acute Otitis Induced by S. pneumoiae, Clinical and Experimental Otorhinolaryngology (Sep. 2012); 5(3):139-144.
Yap et al., "Increase in Methicillin-Resistant *Staphylococcus aureus* Acquisition Rate and Change in Pathogen Pattern Associated with a Outbreak of Severe Acute Respiratory Syndrome," MRSA Increase and Pathogen Shift in SARS (Aug. 2015), CID 2004:39:511-516.
Yuan et al., "Microbiota in viral infection and disease in humans and farm animals," Progress in Molecular Biology and Translational Science (2020); 171:15-60.

Zhang et al., "Prospective study of probiotic supplementation results in immune stimulation and improvement of upper respiratory infection rate," Synthetic and System Biotechnology (2018); 3:113-120.
Lazarini, F., et al., "The microbiome-nose-brain axis in health and disease" Trends Neurosci. Aug. 31, 2022: S0166-2236(22)00160-6. doi: 10.1016/j.tins.2022.08.003.
Mostolizadeh, R., et al., "Towards the human nasal microbiome: Simulating D. pigrum and *S. aureus*" Frontiers in Cellular and Infection Microbiology, vol. 12, Oct. 2022, DOI=10.3389/fcimb.2022.925215, https://doi.org/10.3389/fcimb.2022.925215.
Endam, L. et al., "Intranasal Application of Lactococcus lactis W136 Is Safe in Chronic Rhinosinusitis Patients with Previous Sinus Surgery" (2020). Frontiers in Cellular and Infection Microbiology. 10.3389/fcimb.2020.00440.
Lambert, P.A., et al., "Microbiomics of irrigation with xylitol or Lactococcus lactis in chronic rhinosinusitis. Laryngoscope Investig Otolaryngol" Jan. 21, 2021;6(1):64-70. doi: 10.1002/lio2.524. PMID: 33614931; PMCID: PMC7883620.
Penela-Sanchez, D., et al., "Impact Of The Bacterial Nasopharyngeal Microbiota On The Severity Of Genus Enterovirus Lower Respiratory Tract Infection In Children: A Case-Control Study" Authorea. Dec. 5, 2022. https://www.authorea.com/doi/full/10.22541/au.167023559.91315273/v1.
ATCC catalogue online. Product sheet for strain 10700 retrieved from www.qtcc.org Mar. 28, 2022, 5 pages.
JCM Catalog on line. Product sheet for strain JCM retrieved from www.jcm.riken.jp Mar. 28, 2022, 1 page.
Armbruster, C. R., et al., "Low diversity and instability of the sinus microbiota over time in adults with cystic fibrosis," doi: https://doi.org/10.1101/2022.01.18.476814.
Gladysheva, I., V., et al. "Genome Characterization and Probiotic Potential of Corynebacterium amycolatum Human Vaginal Isolates." Microorganisms. 2022; 10(2):249. https://doi.org/10.3390/microorganisms10020249.
Horn, Kadi J., et al. "*Corynebacterium* species inhibit *Streptococcus pneumoniae* colonization and infection of the mouse airway." Front Microbiol. Jan. 10, 2022;12:804935. doi: 10.3389/fmicb.2021.804935.
Islam, MD., A., et al., "Dolosigranulum pigrum Modulates Immunity against SARS-CoV-2 in Respiratory Epithelial Cells," Pathogens. May 21, 2021;10(6):634, 11 pages. doi: 10.3390/pathogens10060634.

* cited by examiner

AIRWAY MEDICAMENTS

CROSS REFERENCE

This application is a Continuation of International Application No. PCT/US2021/034464 filed on May 27, 2021, which claims the benefit of U.S. Provisional Application No. 62/704,770, filed May 28, 2020, the disclosures of which are incorporated herein by reference in their entirety.

BACKGROUND

Host and environmental factors influence the integrity of the microbiome in subjects. Microbial imbalance can lead to inflammation (or vice versa), resulting in opportunistic pathogenic microorganism colonization and subsequent disease conditions. Probiotic bacteria provide a therapeutic opportunity for addressing microbiome imbalance and disease related conditions. Typically, probiotic bacteria in clinical development to date have focused on gut colonizing bacteria. In some instances, there may be a need for forms of intervention which promote an improved microbiome environment in the upper respiratory tract, in particular the nasal cavity, for the treatment and prevention of conditions in the nasal cavity as well as in systems linked to the upper respiratory tract by a shared mucosal network, such as the lower respiratory tract and central nervous system. In addition, side effects of many current therapies (e.g., chemotherapy and radiation therapy) can increase inflammation and harm the microbiome of the airway system.

BRIEF SUMMARY

Provided herein are compositions, including pharmaceutical compositions, methods, kits and devices for modification of microbiome in a subject. As described in more detail herein, such compositions provide for, among other things, defending the integrity of the nasal cavity microbiome, and beneficially imparting downstream effects on the upper respiratory tract (including the nasal cavity), lower respiratory tract (including the lung), and central nervous system (including the olfactory system) for the prevention and/or treatment of disease conditions. Further provided herein are mixtures of live, purified bacterial strains affording various bactericidal mechanisms to pathogenic bacteria, and in some instances the live, purified bacteria are mutualistic in their relationship to each other. In some embodiments, the live, purified bacteria are selected from *Corynebacterium* species and, optionally, *Dolosigranulum* species. In some embodiments, the live, purified bacteria are species of *Corynebacterium* and/or *Dolosigranulum*. In some embodiments, the live, purified bacteria comprise a strain listed in Table 1 and/or Table 2. In some embodiments, the *Corynebacterium* species is *C. pseudodiphtheriticum, C. accolens, C. amycolatum, C. propinquum, C. glutamicum*, or *C. striatum*. In some embodiments, the *Corynebacterium* species is a combination of at least two species selected from *C. pseudodiphtheriticum, C. accolens, C. amycolatum, C. propinquum, C. glutamicum*, and *C. striatum*. In some embodiments, the *Corynebacterium* species is *C. pseudodiphtheriticum*. In some embodiments, the composition comprises at least two strains of *C. pseudodiphtheriticum*. In some embodiments, the *Corynebacterium* species is *C. pseudodiphtheriticum* and the *Dolosigranulum* species is *D. pigrum*. Further provided herein are compositions wherein the live, purified bacteria comprise bacteria having a high percent identity, e.g., at least 97% identity, based on comparison to whole genome, the entire 16S rRNA region, or a hypervariable region of the 16S rRNA (e.g., V4 region), to a bacterial strain listed in Table 1 or Table 2.

DETAILED DESCRIPTION

Figure 1:
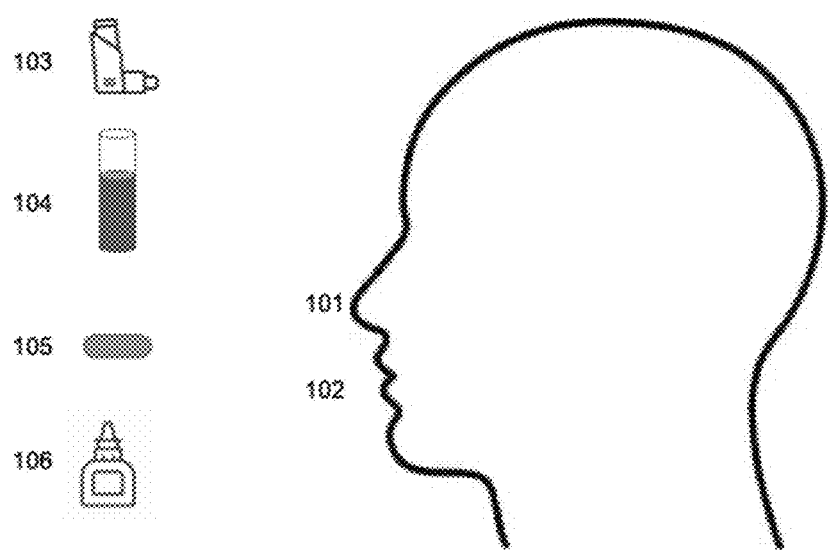
FIG. 1: Illustrates, in some embodiments, various dosage forms described herein for oral 101 and/or intranasal 102 administration. Dosage forms illustrated include an inhaler 103 for aerosol administration, liquid 104 and capsule 105 for oral administration, and a spray bottle 106 for intranasal administration.

Provided herein are composition, methods, kits and devices relating to upper respiratory tract colonizing bacteria for prevention and/or treatment of respiratory tract conditions and/or neurological conditions. Furthermore, provided herein are (1) probiotic bacterial mixtures (2) excipients, dosage forms and routes of administration for such mixtures, (3) and conditions for treatment with such probiotic bacterial mixtures.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included, unless the context clearly dictates otherwise.

The terminology used herein is for the purpose of describing particular instances only and is not intended to be limiting of any embodiment. As used herein, the singular forms "a," "an" and "the" are intended to include the plural forms as well, unless the context clearly indicates otherwise. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The term "subject" as used herein includes human and non-human mammals, including for example: a primate, cow, horse, pig, sheep, goat, dog, cat, or rodent, capable of being colonized by other organisms.

In some embodiments, provided herein are compositions which include bacteria having a percent identity based on 16S rRNA bacterial genetic sequence, a hypervariable region of the 16S rRNA, or whole genome comparison to a reference strain. Typically, comparison of the 16S rRNA bacterial genetic sequence allows a strain to be identified as within the same species as another strain by comparing sequences with known bacterial DNA sequences using NCBI BLAST search. The level of identity in relation to a nucleotide sequence may be determined for at least 20 contiguous nucleotides, for at least 30 contiguous nucleotides, for at least at least 40 contiguous nucleotides, for at least 50 contiguous nucleotides, for at least 60 contiguous nucleotides, or for at least 100 contiguous nucleotides. In some embodiments, the level of identity in relation to a nucleotide sequence is determined for the entire sequence searched. Percent identity may be at least 70%, 80%, 85%, 90%, 91%, 92%, 93%, 94%, 95%, 96%, 97%, 98%, 99%, or 100% to a reference bacterial 16S rRNA sequence, 16S rRNA V4 region sequence, or whole genome sequence. Percent identity may be at least 70%, 80%, 85%, 90%, 91%, 92%, 93%, 94%, 95%, 96%, 97%, 98%, 99%, or 100% to a reference bacteria 16S rRNA: V1 region, V2 region, V3 region, V5 region, V6 region, V7 region, V8 region or V9 region sequence.

In some embodiments, a live bacterium can comprise a bacterium that retains membrane stability. In some embodiments, a live bacterium can comprise a bacterium that is capable of transcription and translation. In some embodiments, a live bacterium can comprise a bacterium that is capable of cell division. In some embodiments, live bacteria can be determined by a culture dependent or a culture independent technique. In some cases, live bacteria can comprise an individual or a group of bacteria that can produce a colony-forming unit (cfu) when plated on stable growth media. In some embodiments, live and/or dead bacteria can be determined by imaging, for example with a live/dead stain. In some embodiments, a viability PCR based method can be used to determine live bacteria. In some cases, a metabolomic assay can be used to determine live bacteria.

In some embodiments, reference to a population of bacteria or a purified population refers to a plurality of bacteria.

1) Probiotic Bacterial Mixtures

The nasal cavity of the upper respiratory tract is a nutrient-poor, high-salinity niche where bacteria compete for limited resources. A healthy nasal microbiome prevents pathogenic microorganisms from colonization, harmful products from such colonization, inflammation, and generation of "leaky" cell-cell junctions, all of which can result in subsequent disease conditions in other organs along a shared mucosal network, including the lungs and central nervous system (CNS). With regard to CNS, many neurological disorders are associated with olfactory system functional impairment, such as loss of smell. The olfactory nerve (cranial nerve I) is the shortest cranial nerve, where cell bodies of primary olfactory neurons are found in the neuroepithelium and their dendrites extend into the nasal cavity. Injury to the olfactory epithelium, such as through pathogen- or chemical-induced damage, can lead to removal of the protective mucosal barrier and death of olfactory neurons, resulting in open channels from the olfactory epithelium to the bulb, creating an avenue for pathogens or their produces materials to sidestep the blood brain barrier. Thus, the nasal cavity provides an opportunity for imparting beneficial microbiome change to prevent and/or treat many disease conditions. For example, in a small human trial, a beneficial strain of *Corynebacterium pseudodiphtheriticum* (*C. pseudodiphtheriticum* strain "090104") has been reported to show efficacy in elimination of *Staphylococcus aureus* from the nasal cavity in volunteers exposed to abnormal microclimate and altered gaseous environment, Kiryukhina et al. *Probiotics and Antimicrobial Proteins* (2013). Nasal spray application of the strain eradicated *S. aureus* in three subjects and reduced its presence in a methicillin-resistant *S. aureus* (MRSA) carrier.

Bacteria described herein are to be used to control, treat, reduce, eliminate, and/or prevent pathogenic colonization by an organism on a subject and/or reduce inflammation. Compositions described herein may be administered or designed for delivery to particular locations of the subject, in particular, the upper respiratory tract, including the anterior nares, nasal cavity, and/or nasopharynx. Bacterial strains described herein may be isolated from the upper respiratory tract regions including, without limitation, anterior nares, nasal cavity, and/or nasopharynx.

In some embodiments, provided herein are compositions having bacterial populations having one or more species, and one or more strains for each of the one or more species. In some instances, a composition described herein includes 1, 2, 3, 4, 5, 6, 7, 8, 9, 10 or more species of bacteria. In some instances, a composition described herein includes 1, 2, 3, 4, 5, 6, 7, 8, 9, 10 or more strains of bacteria. Further provided herein are bacterial populations comprising at least one species of *Corynebacterium*. Further provided herein are bacterial populations comprising a plurality of species of *Corynebacterium*. *Corynebacterium* are gram-stain-positive bacteria, non-spore forming and nonmotile. Exemplary *Corynebacterium* species for inclusion in compositions described herein include: *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* and *C. xerosis*. In some instances, a composition described herein comprises 1, 2, 3, 4, 5, 6, 7, 8, 9, 10 of the *Corynebacterium* strains listed in Table 1. In some embodiments, a population of bacteria described herein comprises a *Corynebacterium* strain having a 16S rRNA sequence of at least 90, 91, 92, 93, 94, 95, 96, 97, 98, 99, or 100% identity to that of a strain listed in Table 1. In some embodiments, a population of bacteria described herein comprises a *Corynebacterium* strain having a 16S rRNA sequence of at least 97% sequence identity with that of a strain listed in Table 1. The sequence identity may be based on a 16s rRNA sequence, 16s rRNA hypervariable region sequence, such as V4, or whole genome comparison. The population of bacteria may be part of a pharmaceutical composition. The bacteria may be live and purified.

TABLE 1

*Corynebacterium* strains

| Species | Strain name | Reference or Deposit |
| --- | --- | --- |
| C. pseudodiphtheriticum | KPL1989 | GenBank: AXLR01000000 |
| C. pseudodiphtheriticum | DSM44287 | GenBank: GCA_000688415.1 ATCC 10700 |
| C. pseudodiphtheriticum | 090104 | GenBank: AVFF01000000 JCM 1320 |
| C. accolens | KPL1818 | GenBank: AXMA01000001.1 |
| C. accolens | DSM 44278 | ATCC 49725 |
| C. amycolatum | DSM6922 | ATCC 49368 |
| C. amycolatum | DSM1567 | MN175937 |
| C. propinquum | DSM44285 | GCA_000375525.1 |
| C. glutamicum | DSM20300 | ATCC 13032 |
| C. striatum | DSM20668 | ATCC 6940 |

In some embodiments, provided herein are bacterial populations comprising at least one species of *Dolosigranulum*. Further provided herein are bacterial populations comprising a plurality of species of *Dolosigranulum*. In some embodiments, provided herein are populations of bacteria comprising at least one strain of *Dolosigranulum pigrum*. In some instances, a composition described herein comprises 1, 2, 3, 4, 5, 6, 7, 8, 9, 10 of the *D. pigrum* strains listed in Table 2. In some embodiments, a population of bacteria described herein comprises a *D. pigrum* strain having a 16S rRNA sequence of at least 90, 91, 92, 93, 94, 95, 96, 97, 98, 99, or 100% sequence identity to that of a strain listed in Table 2. In some embodiments, a population of bacteria described herein comprises a *D. pigrum* strain having a 16S rRNA sequence of at least 9700 sequence identity with that of a strain listed in Table 2. The sequence identity may be based on a 16s rRNA sequence, 16s rRNA hypervariable region sequence, such as V4, or whole genome comparison. The population of bacteria may be part of a pharmaceutical composition. The bacteria may be live and purified.

TABLE 2

*Dolosigranulum* strains

| Species | Strain name | Reference or Deposit |
| --- | --- | --- |
| D. pigrum | KLP1914 | Brugger et al., BioRxiv (2019). |
| D. pigrum | CDC 39-95 | LaClaire and Facklam, 2000 |
| D. pigrum | CDC 2949-98 | LaClaire and Facklam, 2000 |
| D. pigrum | CDC 4294-98 | LaClaire and Facklam, 2000 |
| D. pigrum | CDC 4420-98 | LaClaire and Facklam, 2000 |
| D. pigrum | CDC 4545-98 | LaClaire and Facklam, 2000 |
| D. pigrum | CDC 4709-98 | LaClaire and Facklam, 2000 |
| D. pigrum | CDC 4199-99 | LaClaire and Facklam, 2000 |
| D. pigrum | CDC 4791-99 | LaClaire and Facklam, 2000 |
| D. pigrum | CDC 4792-99 | LaClaire and Facklam, 2000 |
| D. pigrum | AMBR11 | LMG P-31 124 |
| D. pigrum | AMBR12 | LMG P-31 154 |

Further provided herein are populations of bacteria for colonization to the upper respiratory tract having a combination of strains including strains, from different species. In some embodiments, the populations of bacteria comprise at least one strain of *Corynebacterium*, and at least one strain of *Dolosigranulum*. In some embodiments, the populations of bacteria comprise at least one strain of *C. pseudodiphtheriticum* and at least one strain of *D. pigrum*. In some embodiments, the populations of bacteria comprise at least one strain listed in Table 1, and at least one strain listed in Table 2. In some embodiments, the populations of bacteria comprise at least one strain having a 16S rRNA sequence of at least 9700 sequence identity with that of a strain listed in Table 1, and at least one strain having a 16S rRNA sequence of at least 97% sequence identity with that of a strain listed in Table 2. In further embodiments, 1, 2, 3 or more of the *Corynebacterium* strains are *C. pseudodiphtheriticum* strains. The population of bacteria may be part of a pharmaceutical composition. The bacteria may be live and purified. Compositions described herein may have mixtures of species. The mixtures may be up to 1, 2, 3, 4, 5, 6, 7, 8, 9, 10 or more species and may include species listed in Table 1 and/or Table 2. Such species may be present in equal amounts or varied amounts. In some embodiments, each different species is present in at least 1%, 10%, 15%, 20%, 25%, 30%, 35%, 40%, 45%, 50%, or 100% of the total colony forming units (CFUs) for the total CFUs for the population of bacteria. Compositions described herein may have mixtures of strains within a species. The mixtures may be up to 1, 2, 3, 4, 5, 6, 7, 8, 9, 10 or more strains and may be from a species listed in Table 1 and/or Table 2. Such strains may be present in equal amounts or varied amounts. In some embodiments, different strains are present in at least 10%, 15%, 20%, 25%, 30%, 35%, 40%, 45%, 50%, or 100% of the total colony forming units (CFUs) for the total CFUs for the population of bacteria.

In some embodiments, when administered to a subject, bacterial populations described herein reduce or eliminate colonization in the respiratory tract of pathogenic bacteria. Exemplary respiratory tract pathogenic bacteria include, without limitation, *Staphylococcus aureus, Streptococcus pneumoniae, Pseudomonas aeruginosa*, and *Burkholderia pseudomallei*. Exemplary strains of such pathogenic bacteria are listed in Table 3. Such reduction of pathogenic bacteria may be in the upper respiratory tract or the lower respiratory tract.

TABLE 3

Pathogenic bacteria

| Species | Strain name | Reference |
| --- | --- | --- |
| S. aureus (MRSA) | JE2 | BEI Resources NR-46543 |
| S. aureus (MRSA) | LAC | ATCC BAA-1556 |
| S. aureus (MRSA) | Mu50 | ATCC 700699 |
| S. aureus (MSSA) | 96:308/ USA900 | ATCC BAA-1749 |
| S. pneumoniae | TIGR4 | ATCC BAA-33 |
| S. pneumoniae | M270-8 | ATCC BAA-1659 |
| S. pneumoniae | DBL5 | AF071810 |
| Pseudomonas aeruginosa | | ATCC 27853 |
| Burkholderia pseudomallei | MSHR520 | GenBank: GCA_000583835.1 |

2) Excipients, Dosage Forms and Routes of Administrations

To facilitate administration, pharmaceutical compositions described herein may include one or more pharmaceutically acceptable excipients. Example pharmaceutically acceptable excipients include, without limitation, diluents, adjuvants, excipients, water, oils (including petroleum, animal, vegetable or synthetic oils). Further examples include saline, gum acacia, gelatin, starch paste, talc, keratin, colloidal silica, and urea. Such excipients may include binders such as ethyl cellulose, carboxymethylcellulose, microcrystalline cellulose, or gelatin; excipients such as starch, lactose or dextrins; disintegrating agents such as alginic acid, sodium alginate, Primogel, and cornstarch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of excipients include polyethylene glycol, cyclodextrin, oils, or any other similar liquid carrier that may be formulated into a capsule. Still further examples of excipients include sterile diluents such as water, saline solution, physiological saline, Ringer's solution, isotonic sodium chloride, fixed oils such as synthetic mono or diglycerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents. In some embodiments of the invention, the pharmaceutically acceptable carrier can comprise a growth medium that can support the growth and/or static existence of beneficial bacteria described herein in the context of the pharmaceutical composition prior to administration of the pharmaceutical composition to the subject.

In some instances, a pharmaceutical composition described herein includes materials capable of modifying the physical form of a dosage unit. For example, various dosage forms described herein are illustrated in FIG. 1 for oral 101 and/or intranasal 102 administration. Dosage forms for compositions described herein include a nebulizer or inhaler 103 for aerosol administration, liquid 104 and capsule 105 for oral administration, and a spray bottle 106 for intranasal administration. In some instances, a pharmaceutical composition described herein is located within a nasal spray bottle. In some instances, a pharmaceutical composition described herein is prepared as an aerosol. Aerosols encompass a variety of systems including colloids and pressurized packages. Delivery of a composition in this form may include propulsion of a pharmaceutical composition including the beneficial bacteria described herein through use of liquefied gas or other compressed gas or by a suitable pump system. Aerosols may be delivered in single phase, bi-phasic, or triphasic systems. Compositions, including pharmaceutical compositions, described herein may be formulated depending on the route of administration. Such forms include, without limitation, solutions, suspensions, emulsions, cream, gel, lotion, ointment, tablets, tabs, films, pills, pellets, capsules, capsules including liquids, powders, sustained-release formulations, directed release formulations, lyophylates (freeze dried/lyophilized), emulsions, aerosols, sprays, granules, powders, or syrups. Dosage forms may be, without limitation, liquid, a solid, semisolid, gel, or aerosol. Methods of administration include, but are not limited to, oral, intranasal, or by inhalation. Pharmaceutical compositions described herein may include kits where bacteria described herein are included in a first container (e.g., lyophilized cells), and one or more pharmaceutical acceptable excipients are included in a second container (e.g., water). In some embodiments, provided herein are kits, wherein the kit comprises: a container, wherein the first container comprises live, purified, and lyophilized population of bacteria that comprises: a plurality of strains of *Corynebacterium pseudodiphtheriticum*; and a second container, wherein the second container comprises a pharmaceutically acceptable excipient. In some embodiments, provided herein are kits, wherein the kit comprises: a first container, wherein the first container comprises live, purified, and lyophilized population of bacteria that comprises: a plurality of species of *Corynebacterium*; and a second container, wherein the second container comprises a pharmaceutically acceptable excipient. In some embodiments, provided herein are kits, wherein the kit comprises: a first container, wherein the first container comprises live, purified, and lyophilized population of bacteria that comprises: a plurality of strains of *Dolosigranulum pigrum*; and a second container, wherein the second container comprises a pharmaceutically acceptable excipient. In some embodiments, provided herein are kits, wherein the kit comprises: a first container, wherein the first container comprises live, purified, and lyophilized population of bacteria that comprises: a plurality of strains of *Corynebacterium pseudodiphtheriticum*; and a plurality of strains of *Dolosigranulum pigrum* and; and a second container, wherein the second container comprises a pharmaceutically acceptable excipient. In some embodiments, provided herein are kits, wherein the kit comprises: a first container, wherein the first container comprises live, purified, and lyophilized population of bacteria present in a total amount of at least $10^3$ cfu that comprises: a strain of *Corynebacterium pseudodiphtheriticum*; and a strain of *Dolosigranulum pigrum*; and a second container, wherein the second container comprises a pharmaceutically acceptable excipient. Further provided herein are kits, wherein the live, purified, and lyophilized population of bacteria is present in a total amount of up to $10^{15}$ cfu. Further provided herein are kits, wherein the live, purified, and lyophilized population of bacteria is present in a total amount of $10^3$ to $10^{12}$ cfu.

Dosing may include single or multiple administrations of pharmaceutical compositions described herein. Examples include: multiple times a day, daily, every other day, 1, 2, 3, 5, 6, or 7 times a week, weekly, or less often, a single administration, a course of treatment involving several treatments on a regular or irregular basis, or multiple administrations for a period of time until a diminution of colonization is achieved. In some cases, dosing can occur every day, 2 days, 3 days, 4 days, 5 days, 6 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 1 year, 2 years, or as needed. The dosing regimen, including the regularity of and mode of administration, may be dependent on factors including but not limited to the subject being treated; the severity of the condition; the manner of administration, the stage of colonization, the presence of one or more other conditions such as pregnancy, infancy, or the presence of one or more additional diseases. In some embodiments, the subject is an infant. The infant can be up to 24 months old. In some embodiments, the subject is a child. The child may be 2 years to 21 years old. In some embodiments, the subject is an adult. Adults may be 21 years old or more. In some embodiments, the adult is of advanced age, such as 65 years or older.

Compositions, including pharmaceutical compositions, described herein may comprise a single (unit) dose of bacteria. Compositions described herein may comprise about $10^2$ to about $10^{15}$ colony forming units (cfu) of bacteria or a bacterial strain described herein. Compositions described herein may comprise about: $10^2$ to $10^{12}$ cfu, $10^3$ to $10^{12}$ cfu, $10^3$ to $10^{11}$ cfu, $10^3$ to $10^{10}$ cfu, $10^3$ to $10^9$ cfu, $10^3$ to 10 cfu, $10^3$ to $10^7$ cfu, $10^3$ to $10^6$ cfu, $10^3$ to about $10^5$ cfu, $10^3$ to $10^4$ cfu, $10^4$ to $10^{12}$ cfu, $10^4$ to $10^{11}$ cfu, $10^4$ to $10^{10}$ cfu, $10^4$ to $10^9$ cfu, $10^4$ to $10^8$ cfu, $10^4$ to $10^7$ cfu, $10^4$ to $10^6$ cfu, $10^5$ to $10^{12}$ cfu, $10^5$ to $10^{11}$ cfu, about $10^5$ to about $10^{10}$ cfu, $10^6$ to $10^{12}$ cfu, $10^7$ to $10^{12}$ cfu, $10^8$ to $10^{12}$ cfu, $10^9$ to $10^{12}$ cfu, $10^{10}$ to $10^{12}$ cfu, $10^{11}$ to $10^{12}$ cfu, or 106 to $10^{10}$ cfu of bacteria or a bacterial strain described herein. In some embodiments, compositions comprise about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, or about $10^{12}$ cfu of bacteria or a bacterial strain described herein.

Compositions, including pharmaceutical compositions, described herein may comprise $10^2$ to $10^{15}$ colony forming units (cfu) of bacteria or a bacterial strain described herein per mL. Compositions described herein may comprise about $10^2$ to $10^{12}$ cfu, $10^3$ to $10^{12}$ cfu, $10^3$ to $10^{11}$ cfu, $10^3$ to $10^{10}$ cfu, $10^3$ to $10^9$ cfu, $10^3$ to $10^1$ cfu, $10^3$ to $10^7$ cfu, $10^3$ to $10^6$ cfu, $10^3$ to about $10^5$ cfu, $10^3$ to $10^4$ cfu, $10^4$ to $10^{12}$ cfu, $10^4$ to $10^{11}$ cfu, $10^4$ to $10^{10}$ cfu, $10^4$ to 109 cfu, $10^4$ to 101 Cfu, $10^4$ to $10^7$ cfu, $10^4$ to $10^6$ cfu, $10^5$ to $10^{12}$ cfu, $10^5$ to $10^{11}$ cfu, about $10^5$ to about $10^{10}$ cfu, $10^6$ to $10^{12}$ cfu, $10^7$ to $10^{12}$ cfu, $10^8$ to $10^{12}$ cfu, $10^9$ to $10^{12}$ cfu, $10^{10}$ to $10^{12}$ cfu, $10^{11}$ to $10^{12}$ cfu, or 106 to $10^{10}$ cfu of bacteria or a bacterial strain described herein per mL.

Compositions described herein may comprise may at least about 0.01% by weight, at least about 0.05% by weight, at least about 0.1% by weight, at least about 0.2% by weight, at least about 0.3% by weight, at least about 0.4% by weight, at least about 0.5% by weight, at least about 0.6% by weight, at least about 0.7% by weight, at least about 0.8% by weight, at least about 0.9% by weight, at least about 1.0% by weight, at least about 1.5% by weight, at least about 2.0% by weight, at least about 3.0% by weight, at least about 4.0% by weight, at least about 5.0% by weight, at least about 6.0% by weight, at least about 7.0% by weight, at least about 8.0% by weight, at least about 9.0% by weight, at least about 10.0% by weight, at least about 11.0% by weight, at least about 12.0% by weight, at least about 13.0% by weight, at least about 14.0% by weight, at least about 15.0% by weight, at least about 16.0% by weight, at least about 17.0% by weight, at least about 18.0% by weight, at least about 19.0% by weight, at least about 2.0% by weight, at least about 25.0% by weight, at least about 3.0% by weight, at least about 35.0% by weight, at least about 40.0% by weight, at least about 45.0% by weight, or at least about 50.0% by weight of bacteria or bacterial strain described herein. In some embodiments, compositions can include from 0.01% to 30% by weight, from about 0.01% to 20% by weight, from 0.01% to 5% by weight, from 0.1% to 30% by weight, from 0.1% to 20% by weight, from 0.1% to about 15% by weight, from 0.1% to 10% by weight, from 0.1% to 5% by weight, from 0.2% to 5% by weight, from 0.3% to 5% by weight, from 0.4% to 5% by weight, from 0.5% to 5% by weight, or from 1% to 5% by weight of bacteria or bacterial strain described herein.

Compositions, including pharmaceutical compositions, described herein may comprise a ratio (cfu to cfu) of about: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900 or about 1:1000 of a strain in Table 1 to another strain in Table 1 or a strain in Table 2 to another strain in Table 2. Compositions, including pharmaceutical compositions, described herein may comprise a ratio (cfu to cfu) of about: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900 or about 1:1000 of a strain in Table 1 to a strain in Table 2. Compositions, including pharmaceutical compositions, described herein may comprise a ratio (cfu to cfu) of about: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900 or about 1:1000 of multiple strains of *Corynebacterium* and/or *Dolosigranulum pigrum*.

3) Conditions

In some embodiments, provided herein are compositions for the prevention or treatment of a condition of the respiratory tract. As described in more detail herein, such conditions are of the upper and/or lower respiratory tract. The upper airways or upper respiratory tract generally includes the nose and nasal passages, paranasal sinuses, the pharynx, and the portion of the larynx above the vocal folds (cords). The lower airways or lower respiratory tract generally includes the portion of the larynx below the vocal folds, trachea, and the bronchi, bronchioles, and alveoli, which make up the lungs. These structures pull in air from the upper respiratory system, absorb the oxygen, and release carbon dioxide in exchange. In some embodiments, compositions described comprise beneficial bacteria present in an amount sufficient for a reduction in incidence of colonization of a pathogenic bacteria. In some embodiments, the condition relates to a bacterial infection. Sources for bacterial infections for prevention or treatment with pharmaceutical compositions described herein include, without limitation, *S. aureus* (methicillin-resistant *S. aureus* (MRSA) and methicillin-sensitive *S. aureus* (MSSA)), *S. pneumoniae*, *Pseudomonas aeruginosa*, and *Bordetella pertussis*. Upper respiratory tract conditions for treatment or prevention following administration of composition described herein include, without limitation, allergic rhinitis or non-allergic rhinitis, including acute bacterial rhinosinusitis. Lower respiratory tract conditions for treatment or prevention following administration of composition described herein include, without limitation, asthma, tuberculosis, whooping cough (pertussis), pneumonia (including hospital-acquired pneumonia (HAP), ventilator-associated pneumonia (VAP), and community acquired pneumonia (CAP)), walking pneumonia, and bronchitis, lung cancer, cystic fibrosis, chronic obstructive pulmonary disease (COPD) (e.g., emphysema or chronic bronchitis), idiopathic pulmonary fibrosis (IPF), and interstitial lung disease (ILD). In some embodiments, a pharmaceutical composition described herein is administered to a *S. aureus* positive subject, optionally prior to, receiving a ventilator therapy. In further embodiments, the subject is diagnosed with COVID. In some embodiments, a pharmaceutical composition described herein is administered to a coronavirus (CoV) positive subject (e.g., SARS-CoV-2, SARS-CoV Tor2, and MERS-CoV), optionally prior to, receiving a ventilator therapy. In some embodiments, the asthma is childhood asthma, adult onset asthma, occupational asthma, severe asthma, or seasonal asthma. In some embodiments, the lung cancer is small cell lung cancer or non-small cell lung cancer (NSCLC), including adenocarcinoma, squamous cell carcinoma, or large cell carcinoma. Exemplary lung cancers include, without limitation, primary pulmonary lymphoma, lymphangitic carcinomatosis, epithelioid hemangioendothelioma, or multiple cystic lung disease (MCLD), sarcomatoid carcinoma, adenosquamous carcinoma, salivary gland-type lung carcinoma, large cell neuroendocrine carcinoma, granular cell lung tumour, carcinoids, or atypical carcinoids. In some embodiments, the cancer is a lip cancer, tongue cancer, mouth cancer, oral cavity cancer, oropharyngeal cancer. Example cancers in this region include, without limitation, laryngeal cancer, nasopharyngeal cancer, oral squamous cell carcinoma, oropharyngeal squamous cell carcinoma, otic tumors, salivary gland tumors, and paranasal sinus cancer. In some embodiments, a pharmaceutical composition provided herein is an adjuvant to a treatment of respiratory conditions described herein. In some embodiments, cancer is stage I, II, III or IV. In some embodiments, the cancer is metastatic. In some embodiments, a pharmaceutical composition described herein is an adjuvant to chemotherapy for treatment of cancer. In some embodiments, the cancer is a solid cancer or hematopoietic cancer. Exemplary solid cancers include, without limitation, carcinoma and sarcoma. Exemplary hematopoietic cancers include, without limitation, leukemias, myelomas and lymphomas (including Hodgkin lymphomas, or non-Hodgkin lymphomas (NHLs)). Example chemotherapy agents include, without limitation, etoposide optionally with a platinum agent (cisplatin or carboplatin), 5-fluorouracil (5-FU), paclitaxel, docetaxel, hydroxyurea, methotrexate, bleomycin, and capecitabine. In some embodiments, at least one chemotherapy agent is used. In some embodiments, radiation (ionizing radiation) is administered. In some embodiments, radiation (ionizing radiation) and chemotherapy are administered. Therapies such as chemotherapy and radiation can induce an inflammatory response and compromise integrity of cell-cell junctions resulting in additional disease conditions, such as oral mucositis. In some embodiments, a pharmaceutical composition described herein is administered as an adjuvant with one or more checkpoint inhibitors for treatment of a cancer. Exemplary checkpoint inhibitors include, without limitation, anti-CTLA-4 antibody (e.g., ipilimumab), anti-PD-L1 antibody (e.g., atezolizumab), and anti-PD-1 antibody (e.g., nivolumab and pembrolizumab). In some embodiments, a pharmaceutical composition described herein is administered as treatment for a viral condition, or as an adjuvant to a therapy for treatment of a viral condition. In further embodiments, the virus is a virus of the respiratory tract. Exemplary virus of the respiratory tract include, without limitation, influenza A (e.g., H1N1 and H1N5), influenza B, an adenovirus, respiratory syncytial virus (RSV), enterovirus (EVs), human rhinovirus (HRV), human metapneumovirus (HMPV), human bocavirus (HBoV), coronavirus (CoV) (e.g., SARS-CoV-2, SARS-CoV Tor2, and MERS-CoV), and parainfluenza virus (PIV). Exemplary therapies for viral conditions include, without limitation, oseltamivir, zanamivir, ribavirin, palivizumab, and aspirin. In some embodiments, a pharmaceutical composition described herein is administered to a SARS-CoV-2 positive subject, optionally prior to, receiving a ventilator therapy. In some embodiments, a pharmaceutical composition used to treat or prevent a respiratory condition described herein comprises at least one species (or strain) listed in Table 1 or Table 2, or a mixture listed in Tables 4-7. In some embodiments, a pharmaceutical composition described herein is administered to a subject having a respiratory condition, optionally prior to, receiving a ventilator therapy. In some embodiments, a pharmaceutical composition used to treat or prevent a respiratory condition described herein comprises a strain of *C. pseudodiphtheriticum* and, optionally, a strain of *D. pigrum*. In some embodiments, a method for treating nasal colonization by at least one pathogenic microorganism in a subject is provided, the method comprising the steps of: administering a pharmaceutical composition to the subject, wherein the pharmaceutical composition comprises a *Corynebacterium* strain listed in Table 1, and a *Dolosigranulum* strain listed in Table 2. In some embodiments, a method for treating nasal colonization by at least one pathogenic microorganism in a subject is provided, the method comprising the steps of: administering a pharmaceutical composition to the subject, wherein the pharmaceutical composition comprises a *C. pseudodiphtheriticum* strain listed in Table 1, and a *Dolosigranulum* strain listed in Table 2, or a mixture listed in Tables 4-7. In some embodiments, provided herein are methods for reducing colonization of a subject's anterior nares or nasal cavity by a pathogenic microorganism, the method comprising the steps of: administering to a subject having a pathogenic microorganism in the subject's anterior nares or nasal cavity, a live, purified population of bacteria, wherein the live, purified population of bacteria comprises a plurality of strains of *Corynebacterium pseudodiphtheriticum*. Further provided herein are methods wherein the pathogenic microorganism comprises *Staphylococcus aureus, Streptococcus pneumoniae,* or *Pseudomonas aeruginosa.* Further provided herein are methods wherein the live, purified population of bacteria comprises a mixture listed in Tables 4-7. Further provided herein are methods wherein the live, purified population of bacteria comprises a mixture listed in Tables 4-7. Further provided herein are methods wherein the plurality of strains of *C. pseudodiphtheriticum* comprises JCM 1320 or ATCC 10700. Further provided herein are methods wherein the plurality of strains of *C. pseudodiphtheriticum* comprises JCM 1320 and ATCC 10700. Further provided herein are methods wherein the plurality of strains of *C. pseudodiphtheriticum* comprises strains selected from a strain listed in Table 1. Further provided herein are methods for reducing colonization of a subject's anterior nares or nasal cavity by a pathogenic microorganism, the method comprising the steps of: administering to a subject having a pathogenic microorganism in the subject's anterior nares or nasal cavity, a live, purified population of bacteria, wherein the live, purified population of bacteria comprises a plurality of species of *Corynebacterium*. Further provided herein are methods wherein the plurality of species of *Corynebacterium* comprises *C. accolens, C. pseudodiphtheriticum, C. amycolatum, C. propinquum, C. glutamicum,* or *C. striatum.* Further provided herein are methods wherein the pathogenic microorganism comprises *Staphylococcus aureus, Streptococcus pneumoniae,* or *Pseudomonas aeruginosa.* In some embodiments, provided herein are methods for restoration of a loss of smell, comprising: administering to a subject having an airway inflammatory condition, a live, purified population of bacteria, wherein the live, purified population of bacteria comprises a plurality of species of *Corynebacterium*.

In some embodiments, provided herein are compositions for the prevention or treatment of neurological conditions. In some embodiments, the neurological condition is one associated with deficit in olfactory perception. In some embodiments, a subject having the neurological condition is identified as having a deficit in olfactory perception, e.g., marked by a reduction in capacity for smell. Reduction or loss of smell is a condition associated with disease onset for a variety of neurological conditions involving compromised integrity of cellular and mucosal barriers protecting the CNS, in particular in the microenvironment proximal to the olfactory nerve. In some embodiments, the neurological condition is Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, Creutzfeldt-Jakob disease (CJD), autism spectrum disorder (ASD), posttraumatic stress disorder (PTSD), anxiety, or depression. In some embodiments, the ASD is autistic disorder, pervasive developmental disorder—not otherwise specified (PDD-NOS), Asperger Syndrome, Childhood Disintegrative Disorder (CDD), or Rett Syndrome. In some embodiments, the anxiety is generalized anxiety disorder, obsessive-compulsive disorder, panic disorder, post-traumatic stress disorder, or social phobia. In some embodiments, compositions described comprise beneficial bacteria present in an amount sufficient for a reduction in incidence of colonization of a pathogenic bacteria. In some embodiments, the condition relates to a bacterial infection. Sources for bacterial infections for prevention or treatment with pharmaceutical compositions described herein include, without limitation, *S. aureus* (methicillin-resistant *S. aureus* (MRSA) and methicillin-sensitive *S. aureus* (MSSA)), *S. pneumoniae, Pseudomonas aeruginosa, Bordetella pertussis*, and *Burkholderia pseudomallei* (associated with melioidosis). In some embodiments, a pharmaceutical composition described herein is administered as treatment for a viral condition, or as an adjuvant to a therapy for treatment of a viral condition. In further embodiments, the virus is a virus targeting the respiratory tract. Exemplary viruses targeting the respiratory tract include, without limitation, influenza A (e.g., H1N1 and H1N5), influenza B, an adenovirus, respiratory syncytial virus (RSV), enterovirus (EVs), human rhinovirus (HRV), human metapneumovirus (HMPV), human bocavirus (HBoV), coronavirus (CoV) (e.g., SARS-CoV-2, SARS-CoV Tor2, and MERS-CoV), and parainfluenza virus (PIV). Exemplary therapies for viral conditions include, without limitation, oseltamivir, zanamivir, ribavirin, palivizumab, and aspirin. In some embodiments, a pharmaceutical composition used to treat or prevent a neurological condition described herein comprises at least one species (or strain) listed in Table 1 or Table 2, or a mixture listed in Tables 4-7. In some embodiments, a pharmaceutical composition used to treat or prevent a neurological condition described herein comprises a strain of *C. pseudodiphtheriticum* and, optionally, a strain of *D. pigrum*. In some embodiments, a method for treating nasal colonization by at least one pathogenic microorganism in a subject is provided, the method comprising the steps of: administering a pharmaceutical composition to the subject, wherein the pharmaceutical composition comprises a *Corynebacterium* strain listed in Table 1, and a *Dolosigranulum* strain listed in Table 2, or a mixture listed in Tables 4-7. In some embodiments, a method for treating nasal colonization by at least one pathogenic microorganism in a subject is provided, the method comprising the steps of: administering a pharmaceutical composition to the subject, wherein the pharmaceutical composition comprises a *C. pseudodiphtheriticum* strain listed in Table 1, and a *Dolosigranulum* strain listed in Table 2, or a mixture listed in Tables 4-7.

In some embodiments, provided herein are pharmaceutical compositions, wherein the pharmaceutical compositions comprise: a live, purified population of bacteria, wherein the live, purified population of bacteria comprises a plurality of strains of *Corynebacterium pseudodiphtheriticum*; and a pharmaceutically acceptable excipient. Further provided herein is a pharmaceutical composition, wherein the pharmaceutical composition is formulated for intranasal administration. Further provided herein is a pharmaceutical composition, wherein the pharmaceutical composition is formulated for oral administration. Further provided herein is a pharmaceutical composition, wherein the pharmaceutical composition is in a liquid, solid, semisolid, or aerosol dosage form. Further provided herein is a pharmaceutical composition, wherein the pharmaceutical composition is in a dosage form of a suspension, capsule, gel, tablet, lozenge, pill, or powder. Further provided herein is a pharmaceutical composition, wherein the live, purified population of bacteria is present in a total amount of up to $10^{15}$ cfu. Further provided herein is a pharmaceutical composition, wherein the wherein the live, purified population of bacteria is present in a total amount of at least $10^3$ cfu. Further provided herein is a pharmaceutical composition, wherein the live, purified population of bacteria is present in a total amount of $10^3$ to $10^2$ cfu. Further provided herein is a pharmaceutical composition, wherein the strain of *Corynebacterium pseudodiphtheriticum* is selected from a strain listed in Table 1. Further provided herein is a pharmaceutical composition, wherein the live, purified population of bacteria comprises up to 10 strains. In some embodiments, provided herein is a method, comprising administering to a subject to a subject in need thereof, the pharmaceutical composition described herein, wherein the subject has a respiratory condition. Further provided herein is a method, wherein the respiratory condition is asthma, COPD, rhinitis, lung cancer, MRSA, pneumonia (including hospital-acquired pneumonia (HAP), ventilator-associated pneumonia (VAP), and community acquired pneumonia (CAP)), or cystic fibrosis. In some embodiments, provided herein is use of the pharmaceutical composition described herein in the manufacture of a medicament for the treatment of asthma, COPD, rhinitis, lung cancer, MRSA, (including hospital-acquired pneumonia (HAP), ventilator-associated pneumonia (VAP), and community acquired pneumonia (CAP)), cystic fibrosis, idiopathic pulmonary fibrosis, or interstitial lung disease in a subject. In some embodiments, provided herein is use of the pharmaceutical composition described herein in the manufacture of a medicament for the treatment of Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, or Creutzfeldt-Jakob disease (CJD) in a subject.

In some embodiments, provided herein are pharmaceutical compositions, wherein the pharmaceutical compositions comprise: a live, purified population of bacteria, wherein the live, purified population of bacteria comprises a plurality of species of *Corynebacterium*; and a pharmaceutically acceptable excipient. Further provided herein is a pharmaceutical composition, wherein the pharmaceutical composition is formulated for intranasal administration. Further provided herein is a pharmaceutical composition, wherein the pharmaceutical composition is formulated for oral administration. Further provided herein is a pharmaceutical composition, wherein the pharmaceutical composition is in a liquid, solid, semisolid, or aerosol dosage form. Further provided herein is a pharmaceutical composition, wherein the pharmaceutical composition is in a dosage form of a suspension, capsule, gel, tablet, lozenge, pill, or powder. Further provided herein is a pharmaceutical composition, wherein the live, purified population of bacteria is present in a total amount of up to $10^5$ cfu. Further provided herein is a pharmaceutical composition, wherein the wherein the live, purified population of bacteria is present in a total amount of at least $10^3$ cfu. Further provided herein is a pharmaceutical composition, wherein the live, purified population of bacteria is present in a total amount of $10^3$ to $10^{12}$ cfu. Further provided herein is a pharmaceutical composition, wherein the species of *Corynebacterium* is *C. accolens, C. pseudodiphtheriticum, C. propinquum, C. glutamicum,* or *C. striatum*. Further provided herein is a pharmaceutical composition, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a pharmaceutical composition, wherein the species of *Corynebacterium* is selected from a strain listed in Table 1. Further provided herein is a pharmaceutical composition, wherein the live, purified population of bacteria comprises up to 10 strains. In some embodiments, provided herein is a method, comprising administering to a subject to a subject in need thereof, the pharmaceutical composition described herein, wherein the subject has a respiratory condition. Further provided herein is a method, wherein the respiratory condition is asthma, COPD, rhinitis, lung cancer, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease. In some embodiments, provided herein is use of the pharmaceutical composition described herein in the manufacture of a medicament for the treatment of asthma, COPD, rhinitis, lung cancer, MRSA, (including hospital-acquired pneumonia (HAP), ventilator-associated pneumonia (VAP), and community acquired pneumonia (CAP)), cystic fibrosis, idiopathic pulmonary fibrosis, or interstitial lung disease in a subject. In some embodiments, provided herein is use of the pharmaceutical composition described herein in the manufacture of a medicament for the treatment of Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, Creutzfeldt-Jakob disease (CJD), autism spectrum disorder (ASD), posttraumatic stress disorder (PTSD), anxiety, or depression in a subject. In some embodiments, the ASD is autistic disorder, pervasive developmental disorder—not otherwise specified (PDD-NOS), Asperger Syndrome, Childhood Disintegrative Disorder (CDD), or Rett Syndrome. In some embodiments, the anxiety is generalized anxiety disorder, obsessive-compulsive disorder, panic disorder, post-traumatic stress disorder, or social phobia.

In some embodiments, provided herein are pharmaceutical compositions, wherein the pharmaceutical compositions comprise: a live, purified population of bacteria that comprises: a plurality of strains of *Dolosigranulum pigrum*; and a pharmaceutically acceptable excipient. Further provided herein is a pharmaceutical composition, wherein the pharmaceutical composition is formulated for intranasal administration. Further provided herein is a pharmaceutical composition, wherein the pharmaceutical composition is formulated for oral administration. Further provided herein is a pharmaceutical composition, wherein the pharmaceutical composition is in a liquid, solid, semisolid, or aerosol dosage form. Further provided herein is a pharmaceutical composition, wherein the pharmaceutical composition is in a dosage form of a suspension, capsule, gel, tablet, lozenge, pill, or powder. Further provided herein is a pharmaceutical composition, wherein the live, purified population of bacteria comprises up to 10 strains. In some embodiments, provided herein is a method, comprising administering to a subject to a subject in need thereof, the pharmaceutical composition described herein, wherein the subject has a respiratory condition. Further provided herein is a method, wherein the respiratory condition is asthma, COPD, rhinitis, lung cancer, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease. In some embodiments, provided herein is use of the pharmaceutical composition described herein in the manufacture of a medicament for the treatment of asthma, COPD, rhinitis, lung cancer, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease in a subject. In some embodiments, provided herein is use of the pharmaceutical composition described herein in the manufacture of a medicament for the treatment of Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, Creutzfeldt-Jakob disease (CJD), autism spectrum disorder (ASD), posttraumatic stress disorder (PTSD), anxiety, or depression in a subject. In some embodiments, the ASD is autistic disorder, pervasive developmental disorder—not otherwise specified (PDD-NOS), Asperger Syndrome, Childhood Disintegrative Disorder (CDD), or Rett Syndrome. In some embodiments, the anxiety is generalized anxiety disorder, obsessive-compulsive disorder, panic disorder, post-traumatic stress disorder, or social phobia.

In some embodiments, provided herein are pharmaceutical compositions, wherein the pharmaceutical compositions comprise: a live, purified population of bacteria that comprises: a plurality of strains of *Corynebacterium pseudodiphtheriticum*; and at least one strain of *Dolosigranulum pigrum*; and a pharmaceutically acceptable excipient. Further provided herein is a pharmaceutical composition, wherein the pharmaceutical composition is formulated for intranasal administration. Further provided herein is a pharmaceutical composition, wherein the pharmaceutical composition is formulated for oral administration. Further provided herein is a pharmaceutical composition, wherein the pharmaceutical composition is in a liquid, solid, semisolid, or aerosol dosage form. Further provided herein is a pharmaceutical composition, wherein the pharmaceutical composition is in a dosage form of a suspension, capsule, gel, tablet, lozenge, pill, or powder. Further provided herein is a pharmaceutical composition, wherein the live, purified population of bacteria is present in a total amount of up to $10^{15}$ cfu. Further provided herein is a pharmaceutical composition, wherein the wherein the live, purified population of bacteria is present in a total amount of at least $10^3$ cfu. Further provided herein is a pharmaceutical composition, wherein the live, purified population of bacteria is present in a total amount of $10^3$ to $10^2$ cfu. Further provided herein is a pharmaceutical composition, wherein the strain of *Corynebacterium pseudodiphtheriticum* is selected from a strain listed in Table 1. Further provided herein is a pharmaceutical composition, wherein the *Dolosigranulum pigrum* is selected from a strain listed in Table 2. Further provided herein is a pharmaceutical composition, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a pharmaceutical composition, wherein the live, purified population of bacteria comprises up to 10 strains. In some embodiments, provided herein is a method, comprising administering to a subject to a subject in need thereof, the pharmaceutical composition described herein, wherein the subject has a respiratory condition. Further provided herein is a method, wherein the respiratory condition is asthma, COPD, rhinitis, lung cancer, MRSA, pneumonia, cystic fibrosis, idiopathic pulmonary fibrosis, or interstitial lung disease. In some embodiments, provided herein is use of the pharmaceutical composition described herein in the manufacture of a medicament for the treatment of asthma, COPD, rhinitis, lung cancer, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease in a subject. In some embodiments, provided herein is use of the pharmaceutical composition described herein in the manufacture of a medicament for the treatment of Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, Creutzfeldt-Jakob disease (CJD), autism, posttraumatic stress disorder (PTSD), anxiety, or depression in a subject. In some embodiments, the ASD is autistic disorder, pervasive developmental disorder—not otherwise specified (PDD-NOS), Asperger Syndrome, Childhood Disintegrative Disorder (CDD), or Rett Syndrome. In some embodiments, the anxiety is generalized anxiety disorder, obsessive-compulsive disorder, panic disorder, post-traumatic stress disorder, or social phobia.

In some embodiments, provided herein are pharmaceutical compositions, wherein the pharmaceutical compositions comprise: a live, purified population of bacteria present in a total amount of at least $10^3$ cfu, and wherein the live, purified population of bacteria comprises: a strain of *Corynebacterium pseudodiphtheriticum*; and a strain of *Dolosigranulum pigrum*; and a pharmaceutically acceptable excipient, wherein the pharmaceutical composition is formulated for intranasal administration. Further provided herein is a pharmaceutical composition, wherein the live, purified population of bacteria is present in a total amount of up to $10^{15}$ cfu. Further provided herein is a pharmaceutical composition, wherein the live, purified population of bacteria is present in a total amount of $10^3$ to $10^2$ cfu. Further provided herein is a pharmaceutical composition, wherein the strain of *Corynebacterium pseudodiphtheriticum* is selected from a strain listed in Table 1. Further provided herein is a pharmaceutical composition, wherein the *Dolosigranulum pigrum* is selected from a strain listed in Table 2. Further provided herein is a pharmaceutical composition, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a pharmaceutical composition, wherein the live, purified population of bacteria comprises up to 10 strains. In some embodiments, provided herein is a method, comprising administering to a subject to a subject in need thereof, the pharmaceutical composition described herein, wherein the subject has a respiratory condition. Further provided herein is a method, wherein the respiratory condition is asthma, COPD, rhinitis, lung cancer, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease. In some embodiments, provided herein is use of the pharmaceutical composition described herein in the manufacture of a medicament for the treatment of asthma, COPD, rhinitis, lung cancer, MRSA, pneumonia (including hospital-acquired pneumonia (HAP), ventilator-associated pneumonia (VAP), and community acquired pneumonia (CAP)), or cystic fibrosis, idiopathic pulmonary fibrosis, or interstitial lung disease in a subject. In some embodiments, provided herein is use of the pharmaceutical composition described herein in the manufacture of a medicament for the treatment of Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, or Creutzfeldt-Jakob disease (CJD) in a subject.

In some embodiments, provided herein is are pharmaceutical compositions, wherein the pharmaceutical compositions comprise: a live, purified population of bacteria present in a total amount of at least $10^3$ cfu, and wherein the live, purified population of bacteria comprises: a strain of *Corynebacterium pseudodiphtheriticum*; and a strain of *Dolosigranulum pigrum*; and a pharmaceutically acceptable excipient, wherein the pharmaceutical composition is formulated for oral administration. Further provided herein is a pharmaceutical composition, wherein the live, purified population of bacteria is present in a total amount of up to $10^{15}$ cfu. Further provided herein is a pharmaceutical composition, wherein the wherein the live, purified population of bacteria is present in a total amount of at least $10^3$ cfu. Further provided herein is a pharmaceutical composition, wherein the live, purified population of bacteria is present in a total amount of $10^3$ to $10^2$ cfu. Further provided herein is a pharmaceutical composition, wherein the strain of *Corynebacterium pseudodiphtheriticum* is selected from a strain listed in Table 1. Further provided herein is a pharmaceutical composition, wherein the *Dolosigranulum pigrum* is selected from a strain listed in Table 2. Further provided herein is a pharmaceutical composition, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a pharmaceutical composition, wherein the live, purified population of bacteria comprises up to 10 strains. In some embodiments, provided herein is a method, comprising administering to a subject to a subject in need thereof, the pharmaceutical composition described herein, wherein the subject has a respiratory condition. Further provided herein is a method, wherein the respiratory condition is asthma, COPD, rhinitis, lung cancer, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease. In some embodiments, provided herein is use of the pharmaceutical composition described herein in the manufacture of a medicament for the treatment of asthma, COPD, rhinitis, lung cancer, MRSA, pneumonia (including hospital-acquired pneumonia (HAP), ventilator-associated pneumonia (VAP), and community acquired pneumonia (CAP)), or cystic fibrosis, idiopathic pulmonary fibrosis, or interstitial lung disease in a subject. In some embodiments, provided herein is use of the pharmaceutical composition described herein in the manufacture of a medicament for the treatment of Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, Creutzfeldt-Jakob disease (CJD), autism spectrum disorder (ASD), posttraumatic stress disorder (PTSD), anxiety, or depression. In some embodiments, the ASD is autistic disorder, pervasive developmental disorder—not otherwise specified (PDD-NOS), Asperger Syndrome, Childhood Disintegrative Disorder (CDD), or Rett Syndrome. In some embodiments, the anxiety is generalized anxiety disorder, obsessive-compulsive disorder, panic disorder, post-traumatic stress disorder, or social phobia.

In some embodiments, provided herein are methods for microbiome modification in a subject, comprising administering to a subject in need thereof. a population of purified, live bacteria comprising at least one strain of bacteria present in an amount sufficient for prevention or treatment of a lung condition, wherein the at least one strain of bacteria is isolated from upper respiratory tract of a donor. In some embodiments, provided herein are methods for treatment of an inflammatory lung condition, comprising administering to a subject having an inflammatory lung condition: a population of purified, live bacteria comprising at least one strain of bacteria present in an amount sufficient for reduction in incidence of colonization of a pathogenic bacterium in the nasal cavity, wherein the at least one strain of bacteria is isolated from upper respiratory tract of a donor. Further provided herein are methods, wherein the pathogenic bacterium comprises *Staphylococcus aureus, Streptococcus pneumoniae*, or *Pseudomonas aeruginosa*. Further provided herein are methods, wherein the pathogenic bacterium a strain listed Table 3. In some embodiments, provided herein are methods for treatment of an airway inflammatory condition, comprising: administering to a subject in need thereof, a live, purified population of bacteria, wherein the live, purified population of bacteria comprises: a plurality of strains of *Corynebacterium pseudodiphtheriticum*; and at least one strain of *Dolosigranulum pigrum*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a pharmaceutical composition comprising a mixture listed in Tables 4-7. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a method, wherein the airway inflammatory condition is asthma, COPD, rhinitis, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease. Further provided herein is a method, wherein the bacterial population is administered intranasally. Further provided herein is a method, wherein the bacterial population is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu.

In some embodiments, provided herein are methods for treatment of a lower respiratory tract condition, comprising: administering to a subject having a lower respiratory tract infection, a live, purified population of bacteria, wherein the live, purified population of bacteria comprises: a strain of *Corynebacterium pseudodiphtheriticum*; and a strain of *Dolosigranulum pigrum*. In some embodiments, provided herein is a method for treating an airway inflammatory condition, comprising: administering to a subject in need thereof, a live, purified population of bacteria, wherein the live, purified population of bacteria comprises: a plurality of strains of *Corynebacterium pseudodiphtheriticum*; and at least one strain of *Dolosigranulum pigrum*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the airway inflammatory condition is asthma, COPD, rhinitis, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease. Further provided herein is a method, wherein the live, purified population of bacteria is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu.

In some embodiments, provided herein are methods for treatment of an airway inflammatory condition, comprising: administering to a subject having an airway inflammatory condition, a live, purified population of bacteria, wherein the live, purified population of bacteria comprises a plurality of species of *Corynebacterium*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum,*

*C. parvum* (*Propionibacterium acnes*), *C. paurometabolum*, *C. propinquum*, *C. pseudodiphtheriticum* (*C. hofmannii*), *C. pseudotuberculosis*, *C. ovis*, *C. pyogenes—Trueperella pyogenes*, *C. renale*, *C. spec*, *C. striatum*, *C. tenuis*, *C. ulcerans*, *C. urealyticum*, or *C. xerosis*. In some embodiments, provided herein is a method for treating an airway inflammatory condition, comprising: administering to a subject in need thereof, a live, purified population of bacteria, wherein the live, purified population of bacteria comprises: a plurality of strains of *Corynebacterium pseudodiphtheriticum*; and at least one strain of *Dolosigranulum pigrum*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the airway inflammatory condition is asthma, COPD, rhinitis, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease. Further provided herein is a method, wherein the live, purified population of bacteria is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^{15}$ cfu. Further provided herein are methods, wherein the live, purified population of bacteria is present in a total amount of $10^3$ to $10^{12}$ cfu.

In some embodiments, provided herein are methods for treatment of an airway inflammatory condition, comprising: administering to a subject having an airway inflammatory condition, a live, purified population of bacteria, wherein the live, purified population of bacteria comprises: a plurality of strains of *Dolosigranulum pigrum*. In some embodiments, provided herein is a method for treating an airway inflammatory condition, comprising: administering to a subject in need thereof, a live, purified population of bacteria, wherein the live, purified population of bacteria comprises: a plurality of strains of *Corynebacterium pseudodiphtheriticum*; and at least one strain of *Dolosigranulum pigrum*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a method, wherein the airway inflammatory condition is asthma, COPD, rhinitis, MRSA, pneumonia (including hospital-acquired pneumonia (HAP), ventilator-associated pneumonia (VAP), and community acquired pneumonia (CAP)), cystic fibrosis, idiopathic pulmonary fibrosis, or interstitial lung disease. Further provided herein is a method, wherein the live, purified population of bacteria is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^{15}$ cfu. Further provided herein are methods, wherein the live, purified population of bacteria is present in a total amount of $10^3$ to $10^{12}$ cfu.

In some embodiments, provided herein are methods for treatment of lung cancer, comprising: administering to a subject having lung cancer a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein is a method, wherein the species of *Corynebacterium* is *C. accolens*, *C. afermentans*, *C. ammoniagenes*, *C. amycolatum*, *C. argentoratense*, *C. aquaticum*, *C. auris*, *C. bovis*, *C. diphtheria*, *C. equi* (now *Rhodococcus equi*), *C. efficiens*, *C. flavescens*, *C. glucuronolyticum*, *C. glutamicum*, *C. granulosum*, *C. haemolyticum*, *C. halofytica*, *C. kroppenstedtii*, *C. jeikeium*, *C. macginleyi*, *C. matruchotii*, *C. minutissimum*, *C. parvum* (*Propionibacterium acnes*), *C. paurometabolum*, *C. propinquum*, *C. pseudodiphtheriticum* (*C. hofmannii*), *C. pseudotuberculosis*, *C. ovis*, *C. pyogenes—Trueperella pyogenes*, *C. urealyticum*, *C. renale*, *C. spec*, *C. striatum*, *C. tenuis*, *C. ulcerans*, *C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the live, purified population of bacteria is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu.

In some embodiments, provided herein are methods for treatment of cancer, comprising: administering to a subject having cancer, a live, purified population of bacteria as an adjuvant therapy, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein is a method, wherein the species of *Corynebacterium* is *C. accolens*, *C. afermentans*, *C. ammoniagenes*, *C. amycolatum*, *C. argentoratense*, *C. aquaticum*, *C. auris*, *C. bovis*, *C. diphtheria*, *C. equi* (now *Rhodococcus equi*), *C. efficiens*, *C. flavescens*, *C. glucuronolyticum*, *C. glutamicum*, *C. granulosum*, *C. haemolyticum*, *C. halofytica*, *C. kroppenstedtii*, *C. jeikeium*, *C. macginleyi*, *C. matruchotii*, *C. minutissimum*, *C. parvum*

(*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the cancer is a solid cancer or a hematopoietic cancer. Further provided herein is a method, wherein the solid cancer is a carcinoma or a sarcoma. Further provided herein is a method, wherein the hematopoietic cancer is a leukemia, myeloma or lymphoma. Further provided herein is a method, wherein the adjuvant therapy is chemotherapy, radiation therapy, or checkpoint inhibitor therapy. Further provided herein is a method, wherein the live, purified population of bacteria is administered before or after administration of the chemotherapy, radiation therapy, or checkpoint inhibitor therapy. Further provided herein is a method, wherein the live, purified population of bacteria is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^{15}$ cfu. Further provided herein are methods, wherein the live, purified population of bacteria is present in a total amount of $10^3$ to $10^{12}$ cfu.

In some embodiments, provided herein are methods for treatment of asthma, comprising: administering to a subject having asthma a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the live, purified population of bacteria is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu.

In some embodiments, provided herein are methods for treatment of a viral infection condition, comprising: administering to a subject having a viral infection a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the viral infection is influenza A, influenza B, an adenovirus, respiratory syncytial virus (RSV), enterovirus (EVs), human rhinovirus (HRV), human metapneumovirus (HMPV), human bocavirus (HBoV), coronavirus (CoV), or parainfluenza virus (PIV). Further provided herein is a method, wherein the live, purified population of bacteria is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^{15}$ cfu. Further provided herein are methods, wherein the live, purified population of bacteria is present in a total amount of $10^3$ to $10^{12}$ cfu.

In some embodiments, provided herein are methods for treatment of idiopathic pulmonary fibrosis, comprising: administering to a subject having idiopathic pulmonary fibrosis a live, purified population of bacteria, wherein the live, purified population of bacteria comprises: at least one species of *Corynebacterium*, optionally at least one strain of

*Corynebacterium pseudodiphtheriticum*; and optionally, at least one strain of *Dolosigranulum pigrum*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum (Propionibacterium acnes), C. paurometabolum, C. propinquum, C. pseudodiphtheriticum (C. hofmannii), C. pseudotuberculosis, C. ovis, C. pyogenes—Trueperella pyogenes, C. urealyticum, C. renale, C. spec, C. striatum, C. tenuis, C. ulcerans, C. urealyticum, or C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the bacterial population is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to 10^15 cfu. Further provided herein are methods, wherein the live, purified population of bacteria is present in a total amount of 10^3 to 10^12 cfu.

In some embodiments, provided herein are methods for treatment of MRSA, comprising: intranasally or orally administering to a subject having MRSA (MRSA-positive) a live, purified population of bacteria, wherein the live, purified population of bacteria comprises: at least one species of *Corynebacterium*, optionally at least one strain of *Corynebacterium pseudodiphtheriticum*; and at least one strain of *Dolosigranulum pigrum*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum (Propionibacterium acnes), C. paurometabolum, C. propinquum, C. pseudodiphtheriticum (C. hofmannii), C. pseudotuberculosis, C. ovis, C. pyogenes—Trueperella pyogenes, C. urealyticum, C. renale, C. spec, C. striatum, C. tenuis, C. ulcerans, C. urealyticum, or C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to 10^15 cfu. Further provided herein are methods, wherein the live, purified population of bacteria is present in a total amount of 10^3 to 10^12 cfu.

In some embodiments, provided herein are methods for treatment of MSSA, comprising: intranasally or orally administering to a subject having MSAA (MSSA-positive) a live, purified population of bacteria, wherein the live, purified population of bacteria comprises: at least one species of *Corynebacterium*, optionally at least one strain of *Corynebacterium pseudodiphtheriticum*; and at least one strain of *Dolosigranulum pigrum*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum (Propionibacterium acnes), C. paurometabolum, C. propinquum, C. pseudodiphtheriticum (C. hofmannii), C. pseudotuberculosis, C. ovis, C. pyogenes—Trueperella pyogenes, C. urealyticum, C. renale, C. spec, C. striatum, C. tenuis, C. ulcerans, C. urealyticum, or C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to 10^15 cfu. Further provided herein are methods, wherein the live, purified population of bacteria is present in a total amount of 10^3 to 10^12 cfu.

In some embodiments, provided herein are methods for treatment of pneumonia, comprising: intranasally or orally administering to a subject having pneumonia a live, purified population of bacteria present in an amount of at least 10^3 cfu, wherein the live, purified population of bacteria comprises: at least one species of *Corynebacterium*, optionally at least one strain of *Corynebacterium pseudodiphtheriticum*; and at least one strain of *Dolosigranulum pigrum*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum (Propionibacterium acnes), C. paurometabolum, C. propinquum, C. pseudodiphtheriticum (C. hofmannii), C. pseudotuberculosis, C. ovis, C. pyogenes—Trueperella pyogenes, C. urealyticum, C. renale, C. spec, C. striatum, C. tenuis, C. ulcerans, C. urealyticum, or C. xerosis*. Further provided herein is a method, wherein the strain of *Corynebacterium*

*pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu. Further provided herein are methods wherein the pneumonia is pneumonia is hospital-acquired pneumonia (HAP), ventilator-associated pneumonia (VAP), or community acquired pneumonia (CAP).

In some embodiments, provided herein are methods for treatment of rhinitis, comprising: administering to a subject having rhinitis a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein is a method, wherein the rhinitis is allergic rhinitis or non-allergic rhinitis. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the bacterial population is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu.

In some embodiments, provided herein are methods for treatment of COPD, comprising: administering to a subject having COPD a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the bacterial population is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu.

In some embodiments, provided herein are methods for treatment of cystic fibrosis, comprising: administering to a subject having cystic fibrosis a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7. Further provided herein is a method, wherein the bacterial population is administered intranasally. Further provided herein is a method, wherein the live, purified population of bacteria is administered orally. Further provided herein is a method, wherein the subject is an infant. Further provided herein is a method, wherein the subject is a child. Further provided herein is a method, wherein the subject is an adult. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu.

In some embodiments, provided herein are kits, wherein the kit comprises: a first container, wherein the first container comprises live, purified, and lyophilized population of bacteria that comprises: a plurality of strains of *Corynebacterium pseudodiphtheriticum*; and a second container, wherein the second container comprises a pharmaceutically acceptable excipient. Further provided herein is a kite, wherein the strain of *Corynebacterium pseudodiphtheriticum* is selected from a strain listed in Table 1. Further provided herein are kits, wherein the live, purified, and lyophilized population of bacteria is present in an amount sufficient for treatment of a respiratory condition. Further provided herein are kits, wherein the live, purified, and lyophilized population of bacteria is present in a total amount of up to $10^5$ cfu. Further provided herein are kits, wherein the live, purified, and lyophilized population of bacteria is present in a total amount of $10^3$ to $10^{12}$ cfu.

In some embodiments, provided herein are kits, wherein the kit comprises: a first container, wherein the first container comprises live, purified, and lyophilized population of bacteria that comprises: a plurality of species of *Corynebacterium*; and a second container, wherein the second container comprises a pharmaceutically acceptable excipient. Further provided herein is a kit, wherein the species of *Corynebacterium* is selected from a strain listed in Table 1. Further provided herein are kits, wherein the live, purified, and lyophilized population of bacteria is present in an amount sufficient for treatment of a respiratory condition. Further provided herein are kits, wherein the live, purified, and lyophilized population of bacteria is present in a total amount of up to $10^5$ cfu. Further provided herein are kits, wherein the live, purified, and lyophilized population of bacteria is present in a total amount of $10^3$ to $10^{12}$ cfu.

In some embodiments, provided herein are kits, wherein the kit comprises: a first container, wherein the first container comprises live, purified, and lyophilized population of bacteria that comprises: a plurality of strains of *Dolosigranulum pigrum*; and a second container, wherein the second container comprises a pharmaceutically acceptable excipient. Further provided herein is a kit, wherein the *Dolosigranulum pigrum* is selected from a strain listed in Table 2. Further provided herein are kits, wherein the live, purified, and lyophilized population of bacteria is present in an amount sufficient for treatment of a respiratory condition. Further provided herein are kits, wherein the live, purified, and lyophilized population of bacteria is present in a total amount of up to $10^{15}$ cfu. Further provided herein are kits, wherein the live, purified, and lyophilized population of bacteria is present in a total amount of $10^3$ to $10^{12}$ cfu.

In some embodiments, provided herein are kits, wherein the kit comprises: a first container, wherein the first container comprises live, purified, and lyophilized population of bacteria that comprises: a plurality of strains of *Corynebacterium pseudodiphtheriticum*; and a plurality of strains of *Dolosigranulum pigrum* and; and a second container, wherein the second container comprises a pharmaceutically acceptable excipient. Further provided herein is a kit, wherein the strain of *Corynebacterium pseudodiphtheriticum* is selected from a strain listed in Table 1. Further provided herein is a kit, wherein the *Dolosigranulum pigrum* is selected from a strain listed in Table 2. Further provided herein is a pharmaceutical composition comprising a mixture listed in Tables 4-7. Further provided herein are kits, wherein the live, purified, and lyophilized population of bacteria is present in an amount sufficient for treatment of a respiratory condition. Further provided herein are kits, wherein the live, purified, and lyophilized population of bacteria is present in a total amount of up to $10^{15}$ cfu. Further provided herein are kits, wherein the live, purified, and lyophilized population of bacteria is present in a total amount of $10^3$ to $10^{12}$ cfu.

In some embodiments, provided herein are kits, wherein the kit comprises: a first container, wherein the first container comprises live, purified, and lyophilized population of bacteria present in a total amount of at least $10^3$ cfu that comprises: a strain of *Corynebacterium pseudodiphtheriticum*; and a strain of *Dolosigranulum pigrum*; and a second container, wherein the second container comprises a pharmaceutically acceptable excipient. Further provided herein is a kit, wherein the strain of *Corynebacterium pseudodiphtheriticum* is selected from a strain listed in Table 1. Further provided herein is a kit, wherein the *Dolosigranulum pigrum* is selected from a strain listed in Table 2. Further provided herein are kits, wherein the live, purified, and lyophilized population of bacteria is present in an amount sufficient for treatment of a respiratory condition.

In some embodiments, provided herein are methods for treatment of a neurological condition, comprising: administering to a subject having a neurological condition: a population of purified, live bacteria comprising at least one strain of bacteria present in an amount sufficient for reduction in incidence of colonization of a pathogenic bacterium in the nasal cavity, wherein the at least one strain of bacteria is isolated from upper respiratory tract of a donor. Further provided herein is a method, wherein the pathogenic bacterium comprises *Staphylococcus aureus, Streptococcus pneumoniae, Pseudomonas aeruginosa* or *Burkholderia pseudomallei*. Further provided herein is a method, wherein the pathogenic bacterium a strain listed Table 3. *Corynebacterium pseudodiphtheriticum*; and at least one strain of *Dolosigranulum pigrum*. Further provided herein is a method, wherein the neurological condition is Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, or Creutzfeldt-Jakob disease (CJD). Further provided herein are methods wherein, wherein the subject has a deficit in olfactory perception. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes*—*Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for microbiome modification in a subject, comprising: intranasally administering to a subject in need thereof: a population of purified, live bacteria comprising at least one strain of bacteria present in an amount sufficient for treatment of a neurological condition, wherein the at least one strain of bacteria is isolated from upper respiratory tract of a donor. *Corynebacterium pseudodiphtheriticum*; and at least one strain of *Dolosigranulum pigrum*. Further provided herein is a method, wherein the neurological condition is Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, Creutzfeldt-Jakob disease (CJD), autism spectrum disorder (ASD), posttraumatic stress disorder (PTSD), anxiety, or depression. In some embodiments, the ASD is autistic disorder, pervasive developmental disorder—not otherwise specified (PDD-NOS), Asperger Syndrome, Childhood Disintegrative Disorder (CDD), or Rett Syndrome. In some embodiments, the anxiety is generalized anxiety disorder, obsessive-compulsive disorder, panic disorder, post-traumatic stress disorder, or social phobia. Further provided herein are methods wherein, wherein the subject has a deficit in olfactory perception. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^15 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes*—*Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of a neurological condition, comprising: administering to a subject having a neurological infection, a live, purified population of bacteria, wherein the live, purified population of bacteria comprises: a strain of *Corynebacterium pseudodiphtheriticum*; and a strain of *Dolosigranulum pigrum*. *Corynebacterium pseudodiphtheriticum*; and at least one strain of *Dolosigranulum pigrum*. Further provided herein is a method, wherein the neurological condition is Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, or Creutzfeldt-Jakob disease (CJD). Further provided herein are methods wherein, wherein the subject has a deficit in olfactory perception. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes*—*Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum is selected from a strain listed in Table 2. Further provided herein is a method, wherein the strain of Corynebacterium pseudodiphtheriticum is selected from a strain listed in Table 1, and wherein the Dolosigranulum pigrum is selected from a strain listed in Table 2. Further provided herein is a pharmaceutical composition comprising a mixture listed in Tables 4-7.

In some embodiments, provided herein are methods for treatment of a neurological condition, comprising: administering to a subject having a neurological condition, a live, purified population of bacteria, wherein the live, purified population of bacteria comprises a plurality of species of Corynebacterium. Corynebacterium pseudodiphtheriticum; and at least one strain of Dolosigranulum pigrum. Further provided herein is a method, wherein the neurological condition is Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, Creutzfeldt-Jakob disease (CJD), or autism spectrum disorder (ASD). Further provided herein are methods, wherein the ASD is autistic disorder, pervasive developmental disorder—not otherwise specified (PDD-NOS), Asperger Syndrome, Childhood Disintegrative Disorder (CDD), or Rett Syndrome. Further provided herein are methods wherein, wherein the subject has a deficit in olfactory perception. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of Corynebacterium is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of a neurological condition, comprising: administering to a subject having a neurological condition, a live, purified population of bacteria, wherein the live, purified population of bacteria comprises: a plurality of strains of *Dolosigranulum pigrum. Corynebacterium pseudodiphtheriticum*; and at least one strain of *Dolosigranulum pigrum*. Further provided herein is a method, wherein the neurological condition is Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, or Creutzfeldt-Jakob disease (CJD). Further provided herein are methods wherein, wherein the subject has a deficit in olfactory perception. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^15 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of a neurological condition, comprising: administering to a subject having a neurological condition, a live, purified population of bacteria, wherein the live, purified population of bacteria comprises: a plurality of strains of *Corynebacterium pseudodiphtheriticum*; and at least one strain of *Dolosigranulum pigrum*. Further provided herein is a method, wherein the neurological condition is Parkinson's disease (PD), incidental Lewy body disorder (iLBD), dementia with Lewy bodies (DLB), Alzheimer's disease (AD), multiple system atrophy (MSA), progressive supranuclear palsy (PSP), frontotemporal dementia (FTD), amyotrophic lateral sclerosis (ALS), pure autonomic failure (PAF), schizophrenia, Creutzfeldt-Jakob disease (CJD), autism spectrum disorder (ASD), or posttraumatic stress disorder (PTSD), anxiety, or depression. In some embodiments, the ASD is autistic disorder, pervasive developmental disorder—not otherwise specified (PDD-NOS), Asperger Syndrome, Childhood Disintegrative Disorder (CDD), or Rett Syndrome. In some embodiments, the anxiety is generalized anxiety disorder, obsessive-compulsive disorder, panic disorder, post-traumatic stress disorder, or social phobia. Further provided herein are methods wherein, wherein the subject has a deficit in olfactory perception. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^{15}$ cfu. Further provided herein are methods, wherein the live, purified population of bacteria is present in a total amount of $10^3$ to $10^{12}$ cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of Parkinson's disease, comprising: administering to a subject having Parkinson's disease a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of incidental Lewy body disorder, comprising: administering to a subject having a incidental Lewy body disorder a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^{15}$ cfu. Further provided herein are methods, wherein the live, purified population of bacteria is present in a total amount of $10^3$ to $10^{12}$ cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of dementia with Lewy bodies, comprising: administering to a subject having dementia with Lewy bodies a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of Alzheimer's disease, comprising: administering to a subject having Alzheimer's disease a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of multiple system atrophy, comprising: administering to a subject having multiple system atrophy a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of progressive supranuclear palsy, comprising: administering to a subject having progressive supranuclear palsy a live, purified population of bacteria, wherein the live, purified population of bacteria comprises: at least one species of *Corynebacterium*, optionally at least one strain of

*Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of frontotemporal dementia, comprising: administering to a subject having frontotemporal dementia a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of amyotrophic lateral sclerosis, comprising: administering to a subject having amyotrophic lateral sclerosis a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to 10^5 cfu. Further provided herein are methods, wherein the live, purified population of bacteria is present in a total amount of 10^3 to 10^12 cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of pure autonomic failure, comprising: administering to a subject having pure autonomic failure a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of schizophrenia, comprising: administering to a subject having schizophrenia a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of Creutzfeldt-Jakob disease, comprising: administering to a subject having Creutzfeldt-Jakob disease a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of autism spectrum disorder (ASD), comprising: administering to a subject having ASD a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the ASD is autistic disorder, pervasive developmental disorder—not otherwise specified (PDD-NOS), Asperger Syndrome, Childhood Disintegrative Disorder (CDD), or Rett Syndrome. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^{15}$ cfu. Further provided herein are methods, wherein the live, purified population of bacteria is present in a total amount of $10^3$ to $10^{12}$ cfu. Further provided herein is a method, wherein the species of *Corynebacterium* is *C. accolens*, *C. afermentans*, *C. ammoniagenes*, *C. amycolatum*, *C. argentoratense*, *C. aquaticum*, *C. auris*, *C. bovis*, *C. diphtheria*, *C. equi* (now *Rhodococcus equi*), *C. efficiens*, *C. flavescens*, *C. glucuronolyticum*, *C. glutamicum*, *C. granulosum*, *C. haemolyticum*, *C. halofytica*, *C. kroppenstedtii*, *C. jeikeium*, *C. macginleyi*, *C. matruchotii*, *C. minutissimum*, *C. parvum* (*Propionibacterium acnes*), *C. paurometabolum*, *C. propinquum*, *C. pseudodiphtheriticum* (*C. hofmannii*), *C. pseudotuberculosis*, *C. ovis*, *C. pyogenes*—*Trueperella pyogenes*, *C. urealyticum*, *C. renale*, *C. spec*, *C. striatum*, *C. tenuis*, *C. ulcerans*, *C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of posttraumatic stress disorder (PTSD), comprising: administering to a subject having PTSD a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu. Further provided herein is a method, wherein the species of *Corynebacterium* is *C. accolens*, *C. afermentans*, *C. ammoniagenes*, *C. amycolatum*, *C. argentoratense*, *C. aquaticum*, *C. auris*, *C. bovis*, *C. diphtheria*, *C. equi* (now *Rhodococcus equi*), *C. efficiens*, *C. flavescens*, *C. glucuronolyticum*, *C. glutamicum*, *C. granulosum*, *C. haemolyticum*, *C. halofytica*, *C. kroppenstedtii*, *C. jeikeium*, *C. macginleyi*, *C. matruchotii*, *C. minutissimum*, *C. parvum* (*Propionibacterium acnes*), *C. paurometabolum*, *C. propinquum*, *C. pseudodiphtheriticum* (*C. hofmannii*), *C. pseudotuberculosis*, *C. ovis*, *C. pyogenes*—*Trueperella pyogenes*, *C. urealyticum*, *C. renale*, *C. spec*, *C. striatum*, *C. tenuis*, *C. ulcerans*, *C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of anxiety, comprising: administering to a subject having anxiety a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. In some embodiments, the anxiety is generalized anxiety disorder, obsessive-compulsive disorder, panic disorder, posttraumatic stress disorder, or social phobia. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^{15}$ cfu. Further provided herein are methods, wherein the live, purified population of bacteria is present in a total amount of $10^3$ to $10^{12}$ cfu. Further provided herein is a method, wherein the species of *Corynebacterium* is *C. accolens*, *C. afermentans*, *C. ammoniagenes*, *C. amycolatum*, *C. argentoratense*, *C. aquaticum*, *C. auris*, *C. bovis*, *C. diphtheria*, *C. equi* (now *Rhodococcus equi*), *C. efficiens*, *C. flavescens*, *C. glucuronolyticum*, *C. glutamicum*, *C. granulosum*, *C. haemolyticum*, *C. halofytica*, *C. kroppenstedtii*, *C. jeikeium*, *C. macginleyi*, *C. matruchotii*, *C. minutissimum*, *C. parvum* (*Propionibacterium acnes*), *C. paurometabolum*, *C. propinquum*, *C. pseudodiphtheriticum* (*C. hofmannii*), *C. pseudotuberculosis*, *C. ovis*, *C. pyogenes*—*Trueperella pyogenes*, *C. urealyticum*, *C. renale*, *C. spec*, *C. striatum*, *C. tenuis*, *C. ulcerans*, *C. urealyticum*, or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

In some embodiments, provided herein are methods for treatment of depression, comprising: administering to a subject having depression a live, purified population of bacteria, wherein the live, purified population of bacteria comprises: at least one species of *Corynebacterium*, optionally at least one strain of *Corynebacterium pseudodiphtheriticum*; and optionally, at least one strain of *Dolosigranulum pigrum*. Further provided herein are methods, wherein the live, purified population of bacteria is administered intranasally. Further provided herein are methods, wherein the live, purified population of bacteria is administered orally. Further provided herein are methods, wherein the subject is an infant. Further provided herein are methods, wherein the subject is a child. Further provided herein are methods, wherein the subject is an adult. Further provided herein are methods, wherein the adult is 65 years or older. Further provided herein are methods, wherein the live, purified population of bacteria is present in a total amount of up to $10^5$ cfu. Further provided herein are methods, wherein the live, purified population of bacteria is present in a total amount of $10^3$ to $10^{12}$ cfu. Further provided herein is a method, wherein the species of *Corynebacterium* is *C. accolens, C. afermentans, C. ammoniagenes, C. amycolatum, C. argentoratense, C. aquaticum, C. auris, C. bovis, C. diphtheria, C. equi* (now *Rhodococcus equi*), *C. efficiens, C. flavescens, C. glucuronolyticum, C. glutamicum, C. granulosum, C. haemolyticum, C. halofytica, C. kroppenstedtii, C. jeikeium, C. macginleyi, C. matruchotii, C. minutissimum, C. parvum* (*Propionibacterium acnes*), *C. paurometabolum, C. propinquum, C. pseudodiphtheriticum* (*C. hofmannii*), *C. pseudotuberculosis, C. ovis, C. pyogenes—Trueperella pyogenes, C. urealyticum, C. renale, C. spec, C. striatum, C. tenuis, C. ulcerans, C. urealyticum,* or *C. xerosis*. Further provided herein is a method, wherein the strain of *Corynebacterium pseudodiphtheriticum* is selected from a strain listed in Table 1. Further provided herein is a method, wherein the *Dolosigranulum pigrum* is selected from a strain listed in Table 2. Further provided herein is a method, wherein the strain of *Corynebacterium pseudodiphtheriticum* is selected from a strain listed in Table 1, and wherein the *Dolosigranulum pigrum* is selected from a strain listed in Table 2. Further provided herein is a pharmaceutical composition comprising a mixture listed in Tables 4-7.

EXAMPLES

Example 1: Bacterial Mixtures i. Isolates and mixtures. Described herein are combinations of bacterial strains that can be used in generation of compositions, including pharmaceutical compositions for treatment of respiratory tract conditions. In the mixtures that follow, each of the live, purified strains are present in equal CFU amounts to other live, purified strains in each mixture.

First, mixtures having combinations of two strains are generated. Each mixture includes that two strains of *Corynebacterium* listed in Table 1, where an "X" denotes inclusion, are listed in the 44 mixtures (A1 to A44) in Table 4.

TABLE 4

| Mixture | KPL 1989 | DSM4 4287 | 0901 04 | KPL18 18 | DSM44 278 | DSM6 922 | DSM1 567 | DSM44 285 | DSM20 300 | DSM20 668 |
|---|---|---|---|---|---|---|---|---|---|---|
| A1 | X | X | | | | | | | | |
| A2 | X | | X | | | | | | | |
| A3 | X | | | X | | | | | | |
| A4 | X | | | | X | | | | | |
| A5 | X | | | | | X | | | | |
| A6 | X | | | | | | X | | | |
| A7 | X | | | | | | | X | | |
| A8 | X | | | | | | | | X | |
| A9 | X | | | | | | | | | X |
| A10 | | X | X | | | | | | | |
| A11 | | X | | X | | | | | | |
| A12 | | X | | | X | | | | | |
| A13 | | X | | | | X | | | | |
| A14 | | X | | | | | X | | | |
| A15 | | X | | | | | | X | | |
| A16 | | X | | | | | | | X | |
| A17 | | X | | | | | | | | X |
| A18 | | | X | X | | | | | | |
| A19 | | | X | | X | | | | | |
| A20 | | | X | | | X | | | | |
| A21 | | | X | | | | X | | | |
| A22 | | | X | | | | | X | | |
| A23 | | | X | | | | | | X | |
| A24 | | | X | | | | | | | X |
| A25 | | | | X | X | | | | | |
| A26 | | | | X | | X | | | | |
| A27 | | | | X | | | X | | | |
| A28 | | | | X | | | | X | | |
| A29 | | | | X | | | | | X | |
| A30 | | | | | X | X | | | | |
| A31 | | | | | X | | X | | | |
| A32 | | | | | X | | | X | | |
| A33 | | | | | X | | | | X | |
| A34 | | | | | X | | | | | X |
| A35 | | | | | | X | X | | | |

TABLE 4-continued

| Mixture | KPL 1989 | DSM4 4287 | 0901 04 | KPL18 18 | DSM44 278 | DSM6 922 | DSM1 567 | DSM44 285 | DSM20 300 | DSM20 668 |
|---|---|---|---|---|---|---|---|---|---|---|
| A36 | | | | | | X | | X | | |
| A37 | | | | | | X | | | X | |
| A38 | | | | | | X | | | | X |
| A39 | | | | | | | X | X | | |
| A40 | | | | | | | | | X | |
| A41 | | | | | | | | | | X |
| A42 | | | | | | | | X | X | |
| A43 | | | | | | | | X | | X |
| A44 | | | | | | | | | X | X |

Second, mixtures are made that includes two strains of *D. pigrum* listed in Table 2, where an "X" denotes inclusion, are listed in the 66 mixtures (B1 to B66) in Table 5.

TABLE 5

| Mixture | KLP 1914 | CDC 39-95 | CDC 2949-98 | CDC 4294-98 | CDC 4420-98 | CDC 4545-98 | CDC 4709-98 | CDC 4199-99 | CDC 4791-99 | CDC 4791-99 | AMBR 11 | AMBR 12 |
|---|---|---|---|---|---|---|---|---|---|---|---|---|
| B1 | X | X | | | | | | | | | | |
| B2 | X | | X | | | | | | | | | |
| B3 | X | | | X | | | | | | | | |
| B4 | X | | | | X | | | | | | | |
| B5 | X | | | | | X | | | | | | |
| B6 | X | | | | | | X | | | | | |
| B7 | X | | | | | | | X | | | | |
| B8 | X | | | | | | | | X | | | |
| B9 | X | | | | | | | | | X | | |
| B10 | X | | | | | | | | | | X | |
| B11 | X | | | | | | | | | | | X |
| B12 | | X | X | | | | | | | | | |
| B13 | | X | | X | | | | | | | | |
| B14 | | X | | | X | | | | | | | |
| B15 | | X | | | | X | | | | | | |
| B16 | | X | | | | | X | | | | | |
| B17 | | X | | | | | | X | | | | |
| B18 | | X | | | | | | | X | | | |
| B19 | | X | | | | | | | | X | | |
| B20 | | X | | | | | | | | | X | |
| B21 | | X | | | | | | | | | | X |
| B22 | | | X | X | | | | | | | | |
| B23 | | | X | | X | | | | | | | |
| B24 | | | X | | | X | | | | | | |
| B25 | | | X | | | | X | | | | | |
| B26 | | | X | | | | | X | | | | |
| B27 | | | X | | | | | | X | | | |
| B28 | | | X | | | | | | | X | | |
| B29 | | | X | | | | | | | | X | |
| B30 | | | X | | | | | | | | | X |
| B31 | | | | X | X | | | | | | | |
| B32 | | | | X | | X | | | | | | |
| B33 | | | | X | | | X | | | | | |
| B34 | | | | X | | | | X | | | | |
| B35 | | | | X | | | | | X | | | |
| B36 | | | | X | | | | | | X | | |
| B37 | | | | X | | | | | | | X | |
| B38 | | | | X | | | | | | | | X |
| B39 | | | | | X | X | | | | | | |
| B40 | | | | | X | | X | | | | | |
| B41 | | | | | X | | | X | | | | |
| B42 | | | | | X | | | | X | | | |
| B43 | | | | | X | | | | | X | | |
| B44 | | | | | X | | | | | | X | |
| B45 | | | | | X | | | | | | | X |
| B46 | | | | | | X | X | | | | | |
| B47 | | | | | | X | | X | | | | |
| B48 | | | | | | X | | | X | | | |
| B49 | | | | | | X | | | | X | | |
| B50 | | | | | | X | | | | | X | |
| B51 | | | | | | X | | | | | | X |
| B52 | | | | | | | X | X | | | | |
| B53 | | | | | | | X | | X | | | |
| B54 | | | | | | | X | | | X | | |

TABLE 5-continued

| Mixture | KLP 1914 | CDC 39-95 | CDC 2949-98 | CDC 4294-98 | CDC 4420-98 | CDC 4545-98 | CDC 4709-98 | CDC 4199-99 | CDC 4791-99 | CDC 4791-99 | AMBR 11 | AMBR 12 |
|---|---|---|---|---|---|---|---|---|---|---|---|---|
| B55 | | | | | | | X | | | | X | |
| B56 | | | | | | | X | | | | | X |
| B57 | | | | | | | | X | X | | | |
| B58 | | | | | | | | X | | X | | |
| B59 | | | | | | | | X | | | X | |
| B60 | | | | | | | | X | | | | X |
| B61 | | | | | | | | | X | X | | |
| B62 | | | | | | | | | X | | X | |
| B63 | | | | | | | | | X | | | X |
| B64 | | | | | | | | | | X | X | |
| B65 | | | | | | | | | | X | | X |
| B66 | | | | | | | | | | | X | X |

Third, mixtures of *Corynebacterium* listed in Table 1 are each combined with one of the 12 strains of *D. pigrum* listed in Table 2, where an "X" denotes inclusion, are listed in the 66 mixtures (C1 to C130) in Table 6.

TABLE 6

| Mixture | *Corynebacterium* strain (below) | KLP-1914 | CDC 39-95 | CDC 2949-98 | CDC 4294-98 | CDC 4420-98 | CDC 4545-98 | CDC 4709-98 | CDC 4199-99 | CDC 4791-99 | CDC 4791-99 | AMB R11 | AMB R12 |
|---|---|---|---|---|---|---|---|---|---|---|---|---|---|
| C1 | KPL1989 | X | | | | | | | | | | | |
| C2 | DSM44287 | X | | | | | | | | | | | |
| C3 | 090104 | X | | | | | | | | | | | |
| C4 | KPL1818 | X | | | | | | | | | | | |
| C5 | DSM44278 | X | | | | | | | | | | | |
| C6 | DSM6922 | X | | | | | | | | | | | |
| C7 | DSM1567 | X | | | | | | | | | | | |
| C8 | DSM44285 | X | | | | | | | | | | | |
| C9 | DSM20300 | X | | | | | | | | | | | |
| C10 | DSM20668 | X | | | | | | | | | | | |
| C11 | KPL1989 | | X | | | | | | | | | | |
| C12 | DSM44287 | | X | | | | | | | | | | |
| C13 | 090104 | | X | | | | | | | | | | |
| C14 | KPL1818 | | X | | | | | | | | | | |
| C15 | DSM44278 | | X | | | | | | | | | | |
| C16 | DSM6922 | | X | | | | | | | | | | |
| C17 | DSM1567 | | X | | | | | | | | | | |
| C18 | DSM44285 | | X | | | | | | | | | | |
| C19 | DSM20300 | | X | | | | | | | | | | |
| C20 | DSM20668 | | X | | | | | | | | | | |
| C21 | KPL1989 | | | X | | | | | | | | | |
| C22 | DSM44287 | | | X | | | | | | | | | |
| C23 | 090104 | | | X | | | | | | | | | |
| C24 | KPL1818 | | | X | | | | | | | | | |
| C25 | DSM44278 | | | X | | | | | | | | | |
| C26 | DSM6922 | | | X | | | | | | | | | |
| C27 | DSM1567 | | | X | | | | | | | | | |
| C28 | DSM44285 | | | X | | | | | | | | | |
| C29 | DSM20300 | | | X | | | | | | | | | |
| C30 | DSM20668 | | | X | | | | | | | | | |
| C41 | KPL1989 | | | | X | | | | | | | | |
| C42 | DSM44287 | | | | X | | | | | | | | |
| C43 | 090104 | | | | X | | | | | | | | |
| C44 | KPL1818 | | | | X | | | | | | | | |
| C45 | DSM44278 | | | | X | | | | | | | | |
| C46 | DSM6922 | | | | X | | | | | | | | |
| C47 | DSM1567 | | | | X | | | | | | | | |
| C48 | DSM44285 | | | | X | | | | | | | | |
| C49 | DSM20300 | | | | X | | | | | | | | |
| C50 | DSM20668 | | | | X | | | | | | | | |
| C51 | KPL1989 | | | | | X | | | | | | | |
| C52 | DSM44287 | | | | | X | | | | | | | |
| C53 | 090104 | | | | | X | | | | | | | |
| C54 | KPL1818 | | | | | X | | | | | | | |
| C55 | DSM44278 | | | | | X | | | | | | | |
| C56 | DSM6922 | | | | | X | | | | | | | |
| C57 | DSM1567 | | | | | X | | | | | | | |
| C58 | DSM44285 | | | | | X | | | | | | | |
| C59 | DSM20300 | | | | | X | | | | | | | |
| C60 | DSM20668 | | | | | X | | | | | | | |
| C61 | KPL1989 | | | | | | X | | | | | | |

TABLE 6-continued

| Mixture | Corynebacterium strain (below) | KLP-1914 | CDC 39-95 | CDC 2949-98 | CDC 4294-98 | CDC 4420-98 | CDC 4545-98 | CDC 4709-98 | CDC 4199-99 | CDC 4791-99 | CDC 4791-99 | AMB R11 | AMB R12 |
|---|---|---|---|---|---|---|---|---|---|---|---|---|---|
| C62 | DSM44287 | | | | | | X | | | | | | |
| C63 | 090104 | | | | | | X | | | | | | |
| C64 | KPL1818 | | | | | | X | | | | | | |
| C65 | DSM44278 | | | | | | X | | | | | | |
| C66 | DSM6922 | | | | | | X | | | | | | |
| C67 | DSM1567 | | | | | | X | | | | | | |
| C68 | DSM44285 | | | | | | X | | | | | | |
| C69 | DSM20300 | | | | | | X | | | | | | |
| C70 | DSM20668 | | | | | | X | | | | | | |
| C71 | KPL1989 | | | | | | | X | | | | | |
| C72 | DSM44287 | | | | | | | X | | | | | |
| C73 | 090104 | | | | | | | X | | | | | |
| C74 | KPL1818 | | | | | | | X | | | | | |
| C75 | DSM44278 | | | | | | | X | | | | | |
| C76 | DSM6922 | | | | | | | X | | | | | |
| C77 | DSM1567 | | | | | | | X | | | | | |
| C78 | DSM44285 | | | | | | | X | | | | | |
| C79 | DSM20300 | | | | | | | X | | | | | |
| C80 | DSM20668 | | | | | | | X | | | | | |
| C81 | KPL1989 | | | | | | | | X | | | | |
| C82 | DSM44287 | | | | | | | | X | | | | |
| C83 | 090104 | | | | | | | | X | | | | |
| C84 | KPL1818 | | | | | | | | X | | | | |
| C85 | DSM44278 | | | | | | | | X | | | | |
| C86 | DSM6922 | | | | | | | | X | | | | |
| C87 | DSM1567 | | | | | | | | X | | | | |
| C88 | DSM44285 | | | | | | | | X | | | | |
| C89 | DSM20300 | | | | | | | | X | | | | |
| C90 | DSM20668 | | | | | | | | X | | | | |
| C91 | KPL1989 | | | | | | | | | X | | | |
| C92 | DSM44287 | | | | | | | | | X | | | |
| C93 | 090104 | | | | | | | | | X | | | |
| C94 | KPL1818 | | | | | | | | | X | | | |
| C95 | DSM44278 | | | | | | | | | X | | | |
| C96 | DSM6922 | | | | | | | | | X | | | |
| C97 | DSM1567 | | | | | | | | | X | | | |
| C98 | DSM44285 | | | | | | | | | X | | | |
| C99 | DSM20300 | | | | | | | | | X | | | |
| C100 | DSM20668 | | | | | | | | | X | | | |
| C101 | KPL1989 | | | | | | | | | | X | | |
| C102 | DSM44287 | | | | | | | | | | X | | |
| C103 | 090104 | | | | | | | | | | X | | |
| C104 | KPL1818 | | | | | | | | | | X | | |
| C105 | DSM44278 | | | | | | | | | | X | | |
| C106 | DSM6922 | | | | | | | | | | X | | |
| C107 | DSM1567 | | | | | | | | | | X | | |
| C108 | DSM44285 | | | | | | | | | | X | | |
| C109 | DSM20300 | | | | | | | | | | X | | |
| C110 | DSM20668 | | | | | | | | | | X | | |
| C111 | KPL1989 | | | | | | | | | | | X | |
| C112 | DSM44287 | | | | | | | | | | | X | |
| C113 | 090104 | | | | | | | | | | | X | |
| C114 | KPL1818 | | | | | | | | | | | X | |
| C115 | DSM44278 | | | | | | | | | | | X | |
| C116 | DSM6922 | | | | | | | | | | | X | |
| C117 | DSM1567 | | | | | | | | | | | X | |
| C118 | DSM44285 | | | | | | | | | | | X | |
| C119 | DSM20300 | | | | | | | | | | | X | |
| C120 | DSM20668 | | | | | | | | | | | X | |
| C121 | KPL1989 | | | | | | | | | | | | X |
| C122 | DSM44287 | | | | | | | | | | | | X |
| C123 | 090104 | | | | | | | | | | | | X |
| C124 | KPL1818 | | | | | | | | | | | | X |
| C125 | DSM44278 | | | | | | | | | | | | X |
| C126 | DSM6922 | | | | | | | | | | | | X |
| C127 | DSM1567 | | | | | | | | | | | | X |
| C128 | DSM44285 | | | | | | | | | | | | X |
| C129 | DSM20300 | | | | | | | | | | | | X |
| C130 | DSM20668 | | | | | | | | | | | | X |

Fourth, a mixture of multiple *Corynebacterium* strains from Table 1 is made. In this example, 2, 3, 4, or 5 strains are from difference species of *Corynebacterium* are in the composition. Strains are selected from: *C. pseudodiphtheriticum* ATCC 10700 and/or JCM 1320; *C. amycolatum* ATCC 49358; *C. glutamicum* ATCC 13032; and *C. striatum* ATCC 6940. The compositions may include ATCC 10700 and/or JCM 1320 in addition to the strains from species other than ATCC 10700 and/or JCM 1320.

Fifth, a mixture of two *Corynebacterium pseudodiphtheriticum* strains from Table 1 is made: ATCC 10700 and JCM 1320, "mixture D1."

Sixth, mixture D1 is combined with one of the 12 strains of *D. pigrum* listed in Table 2, where an "X" denotes inclusion, are listed in the 66 mixtures (E1 to E12) in Table 7.

incubated at 28° C. and visually assessed at 24, 72, and 120 hours for the absence or presence of a zone of clearance (ZOC). The absence of a ZOC in the presence of a filter disk indicates that physical contact is necessary for anti-*S. aureus* activity against the corresponding most sensitive *S. aureus* strain.

ii. Conditioned Cell Free Medium (CCFM) Preparation and Disk Diffusion Assays. Clinical isolates that produce contact-independent bactericidal anti-*S. aureus* activity (e.g., from strains listed in Table 1, Table 2, and mixtures from Example 1) are independently cultured in 10 mL BHIT broth overnight at 37° C. with shaking at 190 rpm. Cultures are pelleted by centrifugation, and the supernatant is filter-sterilized with a 2 μm filter (Corning). One-milliliter of sterile supernatant is retained, and the remaining supernatant is concentrated (50×) with ammonium sulfate precipitation.

TABLE 7

| Mixture | Mixture D1 (ATCC 10700 and JCM 1320) | KLP-1914 | CDC 39-95 | CDC 2949-98 | CDC 4294-98 | CDC 4420-98 | CDC 4545-98 | CDC 4709-98 | CDC 4199-99 | CDC 4791-99 | CDC 4791-99 | AMB R11 | AMB R12 |
|---|---|---|---|---|---|---|---|---|---|---|---|---|---|
| E1 | X | X | | | | | | | | | | | |
| E2 | X | | X | | | | | | | | | | |
| E3 | X | | | X | | | | | | | | | |
| E4 | X | | | | X | | | | | | | | |
| E5 | X | | | | | X | | | | | | | |
| E6 | X | | | | | | X | | | | | | |
| E7 | X | | | | | | | X | | | | | |
| E8 | X | | | | | | | | X | | | | |
| E9 | X | | | | | | | | | X | | | |
| E10 | X | | | | | | | | | | X | | |
| E11 | X | | | | | | | | | | | X | |
| E12 | X | | | | | | | | | | | | X |

Seventh mixtures of *Corynebacterium* listed in Table 1 are combined to include at least one strain of each of *C. pseudodiphtheriticum*, *C. accolens*, and *C. amycolatum*. For example: ATCC 10700 and/or JCM 1320 plus ATCC 49725 and ATCC 49368.

iii. Cultivation from frozen stocks. Bacterial strains are grown at 37° C. with 5% CO2. *D. pigrum* strains are cultivated from frozen stocks on BBL Columbia Colistin-Nalidixic Acid (CNA) agar with 5% sheep blood (BD Diagnostics) for 2 days. *Corynebacterium* species are cultivated from frozen stocks on BHI agar (e.g., for *C. pseudodiphtheriticum* and *C. propinquum*) or BHI agar supplemented with 1% Tween 80 (e.g., for *C. accolens*) for 1 day. Resuspensions described below are made by harvesting colonies from agar medium and resuspending in 1× phosphate buffered saline (PBS).

Example 2: MRSA Model Systems i. Contact-Dependent Assays. Clinical isolates of *C. pseudodiphtheriticum* and *D. pigrum* taken from subjects (e.g., from strains listed in Table 1 and Table 2, and mixtures from Example 1) are assayed to determine if anti-*S. aureus* activity is dependent on direct physical contact between the bacteria. Briefly, a sterile 0.2 μm filter disk is placed on top of the BHIT agar (Brain Heart Infusion (BHI) agar (Becton Dickinson)) seeded with one of the *S. aureus* strains provided in Table 3 (JE2, LAC, Mu50, or USA 900). Each clinical isolate in a suspension is individually spotted on top of the filter disk so that none of the cell suspension physically touched the *S. aureus* seeded agar plate. Plates are For heat-treatments, 50 μL aliquots of unconcentrated or 50× CCFM are incubated at 90° C. for 10 minutes, then allowed to cool. For the disk diffusion assays, the *S. aureus* strain that is most sensitive to the corresponding inhibitory activity is cultured on BHI agar overnight at 37° C. The following day, the plate-grown cells are recovered and diluted to 1×10^8 cells/ml (OD600 of 0.1) in BHI broth. A sterile swab is then used to spread the *S. aureus* cell suspension on BHIT agar as a lawn. The plate is allowed to dry in a laminar flow hood for 30 minutes. Next, a sterile 5 mm diffusion disk is placed on top of the *S. aureus* lawn, and 50 μL of unconcentrated CCFM or 50× CCFM is inoculated onto the disk. Plates are incubated at 28° C., and images are taken after 72 hours of incubation.

iii. *S. aureus* Infection and CCFM Treatment of *Galleria mellonella* Caterpillars. *Staphylococcus aureus* strains JE2, LAC, Mu50, or USA 900 are cultured overnight on BHI agar at 37° C. The following day, *S. aureus* cells are recovered and diluted to 1×10^8 cells/ml (OD600=0.1) in PBS. Total CFU are then further adjusted to obtain the required doses; i.e., 10^7 CFU or 10^6 CFU in 5 μL of PBS+0.01% bromophenol dye. For infections, *Galleria mellonella* caterpillars (Vanderhorst Wholesale Inc) are utilized within 1 day of receipt. Caterpillars between 200 and 300 mg are chosen for infection. Briefly, 5 μL of inoculum that contained 10^7 or 10^6 total CFU of *S. aureus* are injected into the last left proleg using a 10 μL glass syringe (Hamilton) fitted with a 31G needle. For caterpillars that are treated with CCFM obtains from strains in Table 1, Table 2, and mixtures from Example 1, the caterpillars are maintained at room temperature for 1 hour following the *S. aureus* injection, then refrigerated at 4° C. for 12 minutes and then injected with 5 µL of freshly prepared 50× CCFM from the clinical isolate (treated) or 50× concentrated BHIT (sham treated). These injections are into the last right proleg. All caterpillars are incubated at 37° C., and survival was monitored over 120 hours. Untouched, and PBS injected caterpillars are included as controls.

iv. Intranasal colonization assay for Methicillin-Resistant *Staphylococcus aureus* in Mice. *Staphylococcus aureus* strains JE2, LAC, Mu50, or USA 900 are cultured at 37° C. in either Todd-Hewitt broth (THB) or on Todd-Hewitt agar (THA) (Difco). Brain Heart Infusion (BHI) (Difco) broth and agar are used to grow *C. pseudodiphtheriticum* and *D. pigrum* strains (e.g., from strains listed in Table 1, Table 2, and Example 1). CD1 mice (Charles River Laboratories, Wilmington, Mass.) are obtained. Mice are inoculated intranasally with 10 µl droplet of the inocula at the indicated concentrations. Mice are administered $1 \times 10^9$ CFU total of the bacteria. CD1 mice are inoculated intranasally with: (i) *C. pseudodiphtheriticum*, (ii) *D. pigrum*, (iii) *C. pseudodiphtheriticum* and *D. pigrum*, or (iv) PBS. After two days, the mice are administered streptomycin-resistant MRSA (JE2, LAC, Mu50, or USA 900) by the intranasal route, and sacrificed after another 2 days. For bacterial enumeration, the mice are euthanized using isoflurane followed by cervical dislocation, and the nasal tissue is homogenized and vortexed for 5 min in PBS, and the homogenate is plated on THA with or without streptomycin after appropriate serial dilutions. Bacterial identification is based on antibiotic resistance patterns, colony morphology, and color.

Example 3: Pneumonia Model Systems i. Growth assay of *S. pneumoniae* in cell-free conditioned liquid medium. After growth in BHI, *D. pigrum* or *C. pseudodiphtheriticum* cells (e.g., from strains listed in Table 1, Table 2, and mixtures from Example 1) are removed with a 0.22-µM sterile filter yielding cell-free conditioned medium (CFCM). The pH of the CFCM is adjusted using 2N H2SO4 and 10M KOH to match that of BHI broth alone within 0.02 pH units. *S. pneumoniae* strains TIGR4, DBL5, and M270-8 (see Table 3) are each grown on BBL Columbia CNA agar with 5% sheep blood for 1 day, harvested with a sterile cotton swab, resuspended to an OD600 of 0.30 in 1× PBS, inoculated at 1:100 into both of *D. pigrum* or *C. pseudodiphtheriticum* CFCM and BHI broth and grown for 19-20 hour at 37° C. in static (*S. pneumoniae*) culture under atmospheric conditions. Growth yield is quantified as OD600 absorbance.

ii. Growth assay for *S. pneumoniae* in conditioned by mono- vs. co-culture medium. *D. pigrum* and *C. pseudodiphtheriticum* strains (e.g., from strains listed in Table 1, Table 2, and mixtures from Example 1) are grown from freezer stocks. Cells are harvested with sterile cotton swabs and resuspended in sterile PBS to an OD600 nm of 0.5. Cells are then spotted in 100 µl of 1:1 mixed resuspension on a polycarbonate membrane on BHI agar medium containing 400 U/mL bovine liver catalase. After 2 days of growth, the polycarbonate membrane with *D. pigrum* and/or *C. pseudodiphtheriticum* is removed from each plate leaving cell-free conditioned agar medium. *S. pneumoniae* is grown overnight on BBL Columbia CNA agar with 5% sheep blood using a sterile cotton swab, a lawn is streaked onto the cell-free conditioned agar medium and allowed to grow for 24 hours. Growth/inhibition is assessed daily and photographically recorded.

iii. Mouse model. 6- to 8-week-old FVB/N mice are orally gavaged with 200 µL of either (i) *C. pseudodiphtheriticum*, (ii) *D. pigrum*, (iii) *C. pseudodiphtheriticum* and *D. pigrum* (e.g., from strains listed in Table 1, Table 2, and mixtures from Example 1), or (iv) sterile water (vehicle) (for the bacteria: $1 \times 10^9$ colony-forming units (CFUs)/mL) immediately before procedure. Pneumonia is induced via direct intratracheal instillation of *Pseudomonas aeruginosa* (ATCC 27853) or *S. pneumoniae* (TIGR4, M270-8, or DBL5). Under isoflurane anesthesia, mice receive a midline cervical incision, and *P. aeruginosa* or *S. pneumoniae* is introduced into the trachea via a 29-gauge syringe. Forty microliters of $4 \times 10^8$ CFUs of bacteria diluted in sterile saline is used. Mice are then held vertically for 5 seconds to enhance the delivery into the lungs. Sham mice are treated identically except that they receive an intratracheal injection of saline. All mice receive antibiotic therapy (gentamicin 0.2 mg/mL, subcutaneously) after the surgery to mimic clinical setting. Animals are killed at either 12 or 24 hours (for acute studies) or followed 7 days for survival. For acute studies, mice receive a single dose of (i) *C. pseudodiphtheriticum*, (ii) *D. pigrum*, or (iii) *C. pseudodiphtheriticum* and *D. pigrum*. For survival studies, mice are treated with (i) *C. pseudodiphtheriticum*, (ii) *D. pigrum*, or (iii) *C. pseudodiphtheriticum* and *D. pigrum* daily for 7 days and receive antibiotic treatment at 0, 12, and 24 hours. Lungs are tested for the presence of *P. aeruginosa* or *S. pneumoniae*.

Example 4: Rhinitis Model System

Female BALB/cA mice 2 months old are used. Animals are fed a standard rodent chow diet in a temperature-controlled room (23 degrees C.) on a 12 hour light/dark cycle. The immune response of the mice is suppressed by subcutaneous injections of hydrocortisone (Hydrocortisone hemisuccinate 100, Polfa, PL, 100 mg/kg/day) at day 0 and day 4. *S. aureus* (JE2, LAC, Mu50, or USA 900) is applied intranasally on day 5. Bacterial treatment is performed on day 10. Forty microliters of $4 \times 10^8$ CFUs of bacteria diluted in sterile saline is used. Mice receive a single dose of (i) *C. pseudodiphtheriticum*, (ii) *D. pigrum*, or (iii) *C. pseudodiphtheriticum* and *D. pigrum* (e.g., from strains listed in Table 1, Table 2, and mixtures from Example 1); or (iv) saline (vehicle). Animals are killed at either 12 or 24 hours or followed 7 days for survival, and tissue samples are taken. Blood and internal organ (e.g., lungs, kidney, liver and spleen) samples are tested for the presence of *S. aureus*; nasal epithelium is tested for carriage of *S. aureus* in control and experimental animals.

Example 5: Allergic Asthma Model System i. Allergic asthma mouse model. Female C57BL/6 mice, aged 6-8 weeks (Charles River), are maintained in laminar flow rooms at constant temperature and humidity, with food and water given ad libitum. Mice are treated with vancomycin and/or neomycin (5 days/week at 12-hr intervals) or with bacteria ((i) *C. pseudodiphtheriticum*, (ii) *D. pigrum*, or (iii) *C. pseudodiphtheriticum* and *D. pigrum* (e.g., from strains listed in Table 1, Table 2, and mixtures from Example 1)) (3 times/week), starting 2 weeks before they are i.v. injected with $5 \times 10^5$ B16 melanoma cells and continuing throughout the experiment.

For depletion of effector cells, mice are i.v. injected with CD3 F(ab')2 fragments (145-2C11 f(ab')2) (BioXcell) at a dose of 50 µg/day for 5 days/week starting 1 day before tumor injection to deplete T cells or are intraperitoneally (i.p.) injected with 500 μg of α-NK1.1 antibody (PK136) (BioXcell) 1 day before tumor injection, followed by injection of 200 μg every 5 days throughout the experiment, to deplete NK cells. The efficacy of cell depletion is verified by staining peripheral blood leukocytes for specific subsets after depletion. In therapeutic experiments, mice are i.v. injected with 5×10^5 B16 melanoma cells and treated starting 7 days after tumor cell injection with antibiotics (vancomycin and neomycin) or probiotics ((i) *C. pseudodiphtheriticum*, (ii) *D. pigrum*, or (iii) *C. pseudodiphtheriticum* and *D. pigrum*) alone or in combination with DTIC, administered i.p. at 70 mg/kg (5 days/week). Mice are weighed twice weekly and euthanized at day 21 after tumor injection to count macroscopic lung metastases.

Example 6: Asthma Model Systems i. Acute asthma model system. Six-week-old female BALB/c mice are sensitized by intraperitoneal (i.p.) administration of an ovalbumin (OVA; 10 μg, grade V; Sigma Chemical Co., St. Louis, Mo., USA) and alum (2.25 mg; Imject, Pierce, Rockford, Ill., USA) mixture. One week after the first sensitization, the mixture is administered a second time. Seven days later, the mice inhale 1% OVA via an ultrasonic sprayer (Nescosonic UN-511; Alfresa, Osaka, Japan) for 30 minutes daily for three successive days (OVA challenge). The mice receive bacteria (i) *C. pseudodiphtheriticum*, (ii) *D. pigrum*, or (iii) *C. pseudodiphtheriticum* and *D. pigrum* (e.g., strains in listed Table 1, Table 2, and mixtures from Example 1); or (iv) PBS (vehicle) in an amount of 1×10^9 colony-forming units/mouse/day, intranasally from one week before primary sensitization to the endpoint of the study. Negative controls received only saline instead of OVA at both sensitizations and airway challenge. Positive controls received nothing more after OVA sensitization.

Clinical evaluations in vivo. Airway hyperresponsiveness (AHR) in response to inhaled methacholine (MeCh; Sigma Chemical Co.), administered 24 hours after OVA challenge, is measured in conscious, unrestrained mice using a barometric whole-body plethysmograph (Buxco; EMKA Technologies, Paris, France). Briefly, mice are placed in a whole-body chamber, and basal readings is obtained for 3 minutes and averaged. Aerosolized saline followed by 5-50 mg/mL MeCh are inhaled for 3 minutes after each MeCh inhalation. Treg cells are depleted using anti-CD25 monoclonal antibody (mAb). Briefly, mice received 250 μg of rat anti-mouse CD25 mAb (clone PC61; eBioscience, San Diego, Calif., USA) i.p. in 400 μL of normal saline one day before 1% OVA challenge. Control mice are injected with 250 μg of rat IgG1 (Sigma Chemical Co.).

Bronchoalveolar lavage (BAL) fluid analysis. After measurement of AHR, the mice are anesthetized by i.p. administration of ketamine-xylazine, and the trachea is immediately exposed. The airways are lavaged through a tracheal cannula, two times with 1-mL aliquots of pyrogen-free saline warmed to 37° C. The recovered lavage fluid is pooled, and the cells are collected by centrifugation (5,000 rpm, 4° C., 5 minutes) and resuspended in 100 mL of cold PBS. The cells are stained with trypan blue to determine viability, and total nucleated cells are counted using a hemocytometer.

For differential BAL cell counts, cytospin preparations are made and stained with Diff-Quik (Sysmex, Takatsukadai, Japan). After the samples are coded, all cytospin preparations are evaluated using an oil immersion microscope (magnification, ×1,000). At least 200 cells are counted per preparation, and the absolute number of each cell type is calculated.

Serum IgG analysis. Serum is obtained from blood taken during exsanguination of the mice after airway measurement, and 100 μL (1/10 dilution in carbonate-bicarbonate buffer) is added to each well of a 96-well plate. An IgE-specific enzyme linked immunosorbent assay (ELISA) is used to quantitate total IgE in the serum, using matching antibody pairs (eBioscience) according to the manufacturer's instructions. For the ELISA, 96-well plates are first coated overnight with rat anti-mouse IgE (10 μL in 100 μL of PBS; PharMingen, San Diego, Calif., USA), rat anti-mouse IgG1 (20 μg in 100 μL of PBS; PharMingen), or rat anti-mouse IgG2a (20 μg in 100 μL of PBS; PharMingen). The remaining binding sites are blocked, and the plates are incubated with 100 μL of diluted serum (1:5 for IgE, 1:10 for IgG1 or IgG2a). After the plate is washed, each of the following is sequentially added, incubated, and removed by washing: OVA (1 μg/100 μL), peroxidase-labeled rabbit anti-OVA Ig (240 ng/100 μL, PharMingen), and 3,3,5,5-tetramethylbenzidine solution (Sigma Chemical Co.). The optical density is measured at 450 nm, and the Ig level is determined relative to that of a reference pool of serum from OVA-sensitized BALB/c mice (assigned a value of 100 experimental units/mL)

Cytokine assays. Commercial preparations of paired antibodies and protein standards for measurements of mouse IL-4, IL-5, IL-13, and IFN-γ (eBioscience) in sera is used to develop ELISAs according to the manufacturer's instructions.

Lymphocyte proliferation assay. After BAL, the mouse spleen is resected. Mouse splenocytes are separated on a Histopaque (Sigma Chemical Co.) gradient, and the collected cells are washed with PBS. RBCs are lysed by gently mixing the cells with 3.6 mL of 0.24% NaCl for 20 seconds, followed by the quick addition of 0.3 mL of 8.7% NaCl and further dilution with PBS. The pellet is suspended in Iscove's Modified Dulbecco's Medium (IMDM), and stored overnight at 4° C. The next morning, the cells are centrifuged at 4° C., suspended in cold PBS, stained with trypan blue, and counted using a hemocytometer.

Splenic T cells are cultured in IMDM supplemented with 25 mM HEPES, 10% (v/v) heat inactivated fetal bovine serum (FBS), 60 mg/L (100 U/mL) penicillin, 100 mg/L streptomycin, and 0.29 g/L L-glutamine. Splenic T cells are adjusted to 1×10^5 cells/200 μL/well, transferred to 96-well plates, and incubated at 37° C. in a humidified 5% CO2 incubator for 72 hours. The cells are stimulated with OVA treatment (100 μg/mL) for 72 hours. At 12 hours before the end of the incubation, 1 μCi of [3H]-thymidine is added to each well. The cells are harvested onto a glass microfiber filter (Simport, Beloeil, Canada), and radioactivity is measured in a liquid scintillation counter. The incorporation during the last 12 hours of culture (counts per minute) is used as an index of proliferation.

Flow cytometry. Mouse Treg cells are collected from the spleen and analyzed for CD4+CD25+Foxp3+ expression using a mouse Treg cell staining kit containing FITC-labeled anti-CD4, APC-labeled anti-CD25, and PE-labeled anti-Foxp3 (eBioscience) according to the manufacturer's instructions. Briefly, prepared cells (1×10^6) are washed by centrifugation with cold PBS, resuspended in 1 mL of fixation/permeabilization solution, and incubated in the dark at 4° C. for 30-60 minutes. The cells are washed once with 2 mL of permeabilization buffer, collected by centrifugation, resuspended in 20 mL of blocking agent with 2% (2 mL)

normal rat serum in permeabilization buffer, and incubated at 4° C. for 15 minutes. Next, 20 mL of fluorochrome-conjugated antibody or isotype control in permeabilization buffer is added, followed by incubation in the dark at 4° C. for 30 minutes. Finally, the cells are washed with 2 mL of permeabilization buffer, resuspended in flow cytometry buffer (PBS with 2% FBS), and analyzed by flow cytometry using a FACSCalibur with CellQuest software (BD Biosciences, Mountain View, Calif., USA).

Lung histopathology. For the histological evaluation of lung tissue, the left lung of each mouse is embedded in paraffin, sectioned to a thickness of 5 μm, and stained with hematoxylin and eosin (H&E) to assess eosinophilic infiltration. Inflammation is scored. The degree of peribronchial and perivascular inflammation is evaluated on a subjective scale of 0-3. Cellular infiltration in five randomly selected fields is assessed under a Zeiss Axiophot microscope (magnification, ×100; Carl Zeiss, Inc., Thornwood, N.Y., USA).

ii. Birch pollen-induced allergic asthma mouse model. Mice receive the following: (i) C. pseudodiphtheriticum, (ii) D. pigrum, or (iii) C. pseudodiphtheriticum and D. pigrum (e.g., from strains listed in Table 1, Table 2, and mixtures from Example 1); or (iv) PBS (vehicle) intranasally, eight times on days 1-4 and 8-11 at $5\times10^8$ CFU bacteria/dose, followed by a 2-week asthma induction protocol with birch pollen extract on alternating days. Effects of preventive treatment are analyzed based on serum antibody levels, bronchoalveolar lavage cell counts, lung histology, lung cytokine levels, and airway hyperreactivity. Colonization and translocation of administered bacteria are assessed by bacterial cell counts in nasal mucosa, fecal samples, cervical lymph nodes, and blood.

Example 7: COPD Model System

COPD is induced by cigarette smoke inhalation of 14 cigarettes per day, twice a day, 7 times/week during 60 days in C57Bl/6 mice. The mice receive bacteria (i) C. pseudodiphtheriticum, (ii) D. pigrum, or (iii) C. pseudodiphtheriticum and D. pigrum (e.g., from strains listed in Table 1, Table 2, and mixtures from Example 1); or (iv) PBS (vehicle) in an amount of $1\times10^8$ colony-forming units/mouse/day, intranasally at the same time. The pro-inflammatory mediators as IL-6, TNF, IL-1β, CXCL1, CXCL8, CXCL10, KC, CXCL9, CXCL11 and anti-inflammatory as IL-10 in bronchoalveolar lavage fluid (BALF) are measured by ELISA. The expression of mRNA of MMP9 and MMP12, NF-1κB, STAT3 and TLR 2, 4 and 9 in lung are analyzed by quantitative RT-PCR. NF-κB is also analyzed by immunolocalization. The lung tissue is for histological and morphometric analysis.

Example 8: Influenza Model System

Seven-week-old female BALB/c mice are purchased from SLC Co., Ltd (Hamamatsu, Japan). Mice are housed at 23-25° C. with a 12 hour light/dark cycle and fed standard laboratory rodent feed (Oriental Yeast, Tokyo, Japan). Mice are randomly divided into a control group (viral infection only) and an three treatment groups (infected mice treated with (i) C. pseudodiphtheriticum, (ii) D. pigrum, or (iii) C. pseudodiphtheriticum and D. pigrum (e.g., from strains listed in Table 1, Table 2, and mixtures from Example 1)). Mice are administered in an amount of $1\times10^8$ colony-forming units/600 μL/mouse/day, intranasally for three days.

The influenza A/PR/8/34 (PR8, H1N1) virus is grown in the allantoic sacs of 11-day-old chicken embryos for 2 days at 34° C. The allantoic fluid is removed and stored at −80° C. The viral titre in allantoic fluid is expressed as the 50% tissue culture infectious dose (TCID50) for PR8. The PR8 viral titre in allantoic fluid is $10^{7.4}$ TCID50/ml.

Mice are infected with the PR8 virus. Briefly, on the day after completion of intranasal administration of treatment bacteria solution for three consecutive days, mice are anaesthetized with an intraperitoneal injection of sodium amobarbital (0.25 mg per mouse) and then infected by dropping 1 μl of PR8 into each nostril (2 μl per mouse). To examine the survival of mice inoculated with the PR8 solution, 10 μl of PBS (20 μl of PBS per mouse) is administered intranasally for 3 days after PR8 inoculation. The morbidity and mortality of infected mice are observed for 2 weeks. Morbidity is assessed by ruffling of the fur, slow movement and decreased body weight.

Mice are anaesthetized with diethyl ether and killed the next day after treatment by exsanguination. Lungs are removed, finely minced and incubated for 90 minutes with 300 U of collagenase (Yakult Honsha Co., Tokyo, Japan) in 15 ml of RPMI 1640 medium (Sigma, Tokyo, Japan). To dissociate the tissue into single cells, collagenase-treated minced lungs are gently tapped into a plastic dish. After removal of debris, erythrocytes are depleted by hypotonic lysis. The cells are washed with RPMI medium supplemented with 100 U of penicillin per ml and 100 mg of streptomycin per ml and then resuspended in a medium supplemented with 10% heat-inactivated foetal calf serum (FCS). Cells are counted using Trypan Blue exclusion and then resuspended at an appropriate concentration of $5\times10^6$ cells per ml.

Isolated lung cells are analyzed for cytotoxic activity in a natural killer (NK) cell cytotoxicity assay. Briefly, YAC-1 cells are first labelled with 3,3'-dioctadecyloxacarbocyanine perchlorate (Dio) (Molecular Probes, Eugene, Oreg., USA), with a concentration of $1.0\times10^6$ cells 5 per μl and kept for 10 min in a CO2 incubator. Dio-labelled YAC-1 cells are then mixed with propidium iodide (PI) (Molecular Probes) at $1.0\times10^6$ cells 10 per ml RPMI PI 500 per μl. Appropriate numbers of lung cells are added to $2\times10^4$ Dio-labelled and PI-stained YAC-1 cells in 96-half-well microtitre plates (Corning, N.Y., USA) in a total volume of 0.1 ml of medium containing 10% FCS. The plates are gently centrifuged for 3 minutes at 750 g and then incubated for 4 hours at 37° C. in 5% CO2. After incubation, the cultured cells are mixed with 400 μl PBS in a tube and then analyzed by flow cytometry.

The lungs are removed on day 4. Total RNA is isolated using a FastPure isolation kit (TaKaRa, Ohtsu, Japan). Reverse transcription is carried out with a PrimeScript RT reagent Kit (TaKaRa). Interferon (IFN)-α, IFN-β, IFN-γ, interleukin (IL)-1β, IL-12, IL-18, tumour necrosis factor (TNF) and monocyte chemotactic protein (MCP)-1 mRNA levels are determined using quantitative RT-PCR. Fluorescent reporters are detected using a Thermal Cycler Dice Real Time System Single (TaKaRa), and primers are designed using the Perfect Real Time support system (TaKaRa). Actin-β mRNA levels are determined for all samples to normalize gene expression. All data are expressed as fold induction compared with those obtained for control mice.

Example 9: Idiopathic Pulmonary Fibrosis (IPF) Model System

Eight to 10-week-old C57BL/6J mice are purchased from The Jackson Laboratory and housed under specific pathogen-free conditions. Germ-free (GF) mice on a C57BL/6 background are bred. Oropharyngeal bleomycin is delivered to mice to elicit acute inflammation (Days 0-7), fibroproliferation (Days 7-14), and fibrosis (Days 14-21). Bleomycin treated mice are randomly divided into a control group (PBS only) and three treatment groups (bleomycin treated with (i) *C. pseudodiphtheriticum*, (ii) *D. pigrum*, or (iii) *C. pseudodiphtheriticum* and *D. pigrum* (e.g., from strains listed in Table 1, Table 2, and mixtures from Example 1)). Mice are intranasally administered three times, i.e. 20 µl treatment bacteria solution at a concentration of 10 mg/ml (200 g per mouse) once daily for three consecutive days. Tissue collection (including lung), processing, staining is performed. Collagen deposition is measured using a hydroxyproline assay. Genomic DNA extraction from mouse lung tissue and human bronchoalveolar lavage fluid is performed. Pulmonary inflammation in vivo is evaluated by cytokine measurements of human BALF and murine lung homogenate using a Luminex platform (MilliporeSigma).

Example 10: Olfactory Nerve Infection Model System

Bacterial strains. The *B. pseudomallei* strain MSHR520 is a clinical isolate from a human case of melioidosis. An allele replacement mutant of MSHR520 lacking capsule (MSHR520ΔCap) is generated. *C. pseudodiphtheriticum* (Table 1) and *D. pigrum* (Table 2) clinical isolates are also prepared.

Mice. S100β-DsRed transgenic reporter mice are obtained in which the human S100β promoter drives expression of the DsRed fluorescent protein such that cells that express the S100β promoter express DsRed in the cytoplasm. In these mice, glial cells including olfactory ensheathing cells (OECs) of the olfactory nerve, and Schwann cells of other peripheral nerves express DsRed protein.

i. Methimazole treatment and intranasal inoculation. 5 to 10 weeks old S100β-DsRed mice are injected with methimazole (Sigma-Aldrich, 50 mg/kg, 10 mg/ml in phosphate buffered saline, PBS) or vehicle (PBS) using intraperitoneal injection. Three days later, animals are intranasally inoculated with MSHR520ΔCap or vehicle. A small amount of frozen stock (−80° C. in 20% glycerol; 10-50 μl) is streaked onto LB agar containing streptomycin (100 μg/ml), incubated at 30° C. for several days, and a single colony is used to inoculate liquid RB broth and grown with shaking for 16 hour to stationary phase at 37° C. A portion is used for viable count (CFU) determination on LB agar to ensure that the inoculum used is, consistently, a total of 3×10^5 cells which are resuspend in PBS and delivered as 10 μl droplet/nostril. *C. pseudodiphtheriticum* and *D. pigrum* isolates D1-D30 are prepared as described in Example 2 and in a total of 1×10^8 cells which are resuspend in PBS and delivered as 10 μl droplet/nostril. Mice are intranasally administered 3 times a day for 3 days: (i) *C. pseudodiphtheriticum*, (ii) *D. pigrum*, (iii) *D. pigrum C. pseudodiphtheriticum*, or (iv) PBS. Five days later, mice are administered: (i) control (PBS injection+PBS inoculation), (ii) methimazole alone (methimazole injection+PBS inoculation), (iii) *B. pseudomallei* alone group (PBS injection+*B. pseudomallei* inoculation), (iv) methimazole+*B. pseudomallei* group (methimazole injection+*B. pseudomallei* inoculation).

Animals are housed in individually ventilated hepa-filtered cages (IsoCage N-Biocontainment, Tecniplast) with Aspen wood chip bedding. Animals are provided ad lib food pellets (Standard Rat and Mouse Feed, Specialty Feeds) and water. Environmental conditions within the cages are maintained at a constant temperature (19-23° C.) and humidity (40-60%) with a 12-hour light and a 12-hour dark cycle.

Tissue preparation. Mice are sacrificed 7 days post intranasal methimazole/*B. pseudomallei* inoculation by lethal intraperitoneal injection of sodium pentobarbitone (Lethabarb). Heads are fixed in 4% paraformaldehyde (PFA) in PBS overnight at 4° C., followed by decalcification in 20% ethylenediaminetetraacetic acid (EDTA) for four weeks. Heads are embedded in optimal cutting temperature (OCT) medium (ProSciTech) and frozen. Coronal sections (50 m) are cut using a cryostat (Leica CM1860).

Immunohistochemistry. Rabbit anti-*B. pseudomallei* (1:2,000) is used to label *B. pseudomallei*. This antibody is raised against the sarkosyl-insoluble fraction enriched for outer membrane proteins (RRID:AB_2736920). The secondary antibody is donkey anti-rabbit Alexa Fluor 488 (Abcam ab150073; 1:300). Class III Beta tubulin is detected with rabbit anti-beta III Tubulin (Abcam ab18207; 1:200); the secondary antibody is donkey anti-rabbit Alexa Fluor 647 (Thermofisher A31573; 1:400). Antibodies are diluted in 2% bovine serum albumin (BSA) with 0.3% Triton X-100 (TX) in PBS. Cryostat sections are first incubated with 2% BSA/TX/PBS for 60 min at room temperature, followed by overnight incubation with primary antibodies at 4° C. Sections are washed and incubated with secondary antibodies for 1 h. Cell nuclei were stained with 4'6-diamidino-2-phenylindole (DAPI). Images are captured using an epifluorescence microscope and a laser scanning confocal microscope. Detection of whether bacteria are present in the olfactory epithelium, olfactory nerve and olfactory bulb, is performed.

Example 11: Autism Spectrum Disorder Model System

Mice. Adult mice (2-4 mo) of both sexes are used. The experimental Cntnap2 and Shank3 mice are obtained by breeding heterozygotes with heterozygotes so that litters including wild-type (WT; +/+), heterozygote (HET; +/−), and homozygote (KO; −/−) mice could be obtained. The original breeder mice are available from the Jackson Laboratory (Bozdagi et al. 2010; Poliak et al. 2003).

AAV-GCaMP6 Injection. AAV2/1.Syn.GCaMP6fWPRE.SV40 (Penn Vector Core; titer ~22×10^13 GC/mL, volume ~0.1 μL) is injected into the dorsal olfactory bulb using a Picospritzer III, according to the method described by Kuhlman and Huang (2008). A glass pipette (tip size ~10 μm) is lowered through a hole in the skull to ~300 μm below the pial surface; 20 pulses (~10 ms long) are pressure injected at 0.3 Hz, and then the pipette is retracted 50 μm toward the surface and injection repeated as before at each site. This sequence is repeated until the pipette reached ~50 μm below the surface. This injection protocol resulted in a widespread and dense GCaMP6 expression in cell bodies and dendritic processes in mitral and tufted cells. Virus is allowed to express for 2 to 3 weeks after injection before craniotomy and imaging is performed.

The WT and KO mice are randomly divided into a control group (PBS only) and three treatment groups: (i) *C. pseudodiphtheriticum*, (ii) *D. pigrum*, or (iii) *C. pseudodiphtheriticum* and *D. pigrum* (e.g., from strains listed in Table 1, Table 2, and mixtures from Example 1). Mice are administered in an amount of 1×10^8 colony-forming units/600 μL/mouse/day, intranasally for three days.

In Vivo Two-Photon Calcium Imaging. Mice are anesthetized with ketamine (20 mg/mL)-xylazine (3.3 mg/mL) followed by supplemental ketamine. Reinjection of ketamine (20 mg/mL) is performed every 30 min to maintain a stable level of anesthesia throughout surgery and imaging (6-7 h). A window (1 mm×1 mm) is created over the left dorsal olfactory bulb of mice and covered by no. 1.5 cover glasses (Zeiss) sealed with dental acrylic. A thin layer of low-melting-point agarose gel is placed in between the craniotomy and the cover glass to reduce motion during imaging. The craniotomy is performed on the same area of the dorsal surface across animals to ensure consistent placing of the craniotomy and thus sampling of glomeruli. Two-photon imaging of dendritic processes in the glomerular layer is performed on head-fixed mice using a Chameleon Ultra II laser tuned to a wavelength of 935 nm and an in vivo two-photon platform from Intelligent Imaging Innovations (3I), through a Zeiss W Plan-apochromatic ×20/1.0 objective. Data analysis of GCaMP6 activity is only performed within individual glomeruli. Because of the widespread expression of GCaMP6 across all layers of main olfactory bulb (MOB), GCaMP6 activity recorded in the superficial glomeruli is considered population activity and potentially attributed by a variety of cell types. Before each odor presentation, a 1-min-long video is captured to assess spontaneous event rate. For each odor presentation trial, a 20-s-long video capturing 5-s baseline and 15-s poststimulus fluorescence activity is collected in Slidebook5.5 (3I) at a frequency of 4.7 Hz. The imaging field is a resolution of 200×200 pixel^2, corresponding to a 520×520-μm^2 window. Positioning of the cranial window under the microscope is consistent so that similar subareas of the dorsal field were viewed across animals.

Odorant Stimulation. Brief pulses of isoamyl acetate (IAA; 100% saturated vapor, flow rate ~7.5 L/min) are delivered to the anesthetized mouse through a custom-built olfactometer to the animal's left nostril. Odor pulses are controlled by valves opened via transistor-transistor logic pulses (Lee Valves). The distance of the tubing outlet to the nostril (~5 mm) is maintained throughout each experiment and across animals. Stimuli consisted of a single-pulse of IAA. In initial tests, stimulus duration is varied between 5 and 1,000 ms. Single-trial responses of multiple glomeruli in the field are obtained for a range of stimulus durations to construct the relation between the stimulus duration and the fraction of activated glomeruli. In a typical experiment, the 200-ms stimulus is presented first followed by the 20-ms stimulus, followed by an interval of 1.5-2 minutes for 15 trials. Photoionization detector (PID) measurements of the odor plume are collected using a MiniRAE 3000 (RAE Systems, Inc., Sunnyvale, Calif.). The PID is placed roughly 5 mm from the end of the tubing. This distance is to mimic the distance from the tubing to the animal's nostril. PID measurements are digitized at 10 kHz using an ITC-18 (InstruTECH) controlled by custom software written in IgorPro (Wavemetrics).

Example 12: Parkinson's Disease Model System 4-week-old and 2-month-old male C57BL/6 mice. Fifteen mice are employed in each group. All the mice are raised without pathogens, randomly fed with food and water, and fed in a 12/12-hour light/dark cycle in a temperature control room (25±2° C.) for 1 week before the experimental manipulation.

The mice receive bacteria (i) *C. pseudodiphtheriticum*, (ii) *D. pigrum*, or (iii) *C. pseudodiphtheriticum* and *D. pigrum* (e.g., strains in listed Table 1, Table 2, and mixtures from Example 1); or (iv) PBS (vehicle) in an amount of 1×10^9 colony-forming units/mouse/day, intranasally from one week before MPTP sensitization to the endpoint of the study. Mice receive MPTP (Sigma, USA) in an amount of (1 mg/nostril). One month after MPTP administration, motor behaviour is analysed by rotarod test and pole test.

Rotarod Test. All sessions are performed in the range (8 and 12 am). To learn how to keep their balance, mice first received a 300 second training session on the slowly rotating rod (16 rpm). 1 hour later, mice are re-placed in the rod, and the time (latency) until a mouse falls off the rod rotating as being continuously accelerated was measured (increased per 30 seconds, from 16 to 32 rpm in 5 minutes). The combined measures of the rotarod performance of each mouse are yielded as the area under the mean time curve on the rod against rotation speed (overall rod performance scores, ORP).

Pole Test. For the assessment of bradykinesia in the mice, a pole test is performed. The mouse is placed on top of a vertical rough-surfaced stick (with a diameter of 10 mm, and a height of 58 cm). The time to turn and reach the floor are recorded. Two days before the test, each mouse is trained to descend the pole. On the day of the test, the mice can practice five times and then three times for up to 4 minute each.

Example 13: Lung Cancer Model System i. Mouse model Female C57BL/6 mice, aged 6-8 weeks (Charles River), are maintained in laminar flow rooms at constant temperature and humidity, with food and water given ad libitum. Mice are treated with vancomycin and/or neomycin (5 days/week at 12-hr intervals) or with bacteria ((i) *C. pseudodiphtheriticum*, (ii) *D. pigrum*, or (iii) *C. pseudodiphtheriticum* and *D. pigrum*) (e.g., strains in listed Table 1, Table 2, and mixtures from Example 1) (3 times/week), starting 2 weeks before they are i.v. injected with 5×10^5 B16 melanoma cells and continuing throughout the experiment.

For depletion of effector cells, mice are i.v. injected with CD3 F(ab')2 fragments (145-2C11 f(ab')2) (BioXcell) at a dose of 50 μg/day for 5 days/week starting 1 day before tumor injection to deplete T cells or are intraperitoneally (i.p.) injected with 500 μg of α-NK1.1 antibody (PK136) (BioXcell) 1 day before tumor injection, followed by injection of 200 μg every 5 days throughout the experiment, to deplete NK cells. The efficacy of cell depletion is verified by staining peripheral blood leukocytes for specific subsets after depletion. In therapeutic experiments, mice are i.v. injected with 5×10^5 B16 melanoma cells and treated starting 7 days after tumor cell injection with antibiotics (vancomycin and neomycin) or probiotics ((i) *C. pseudodiphtheriticum*, (ii) *D. pigrum*, or (iii) *C. pseudodiphtheriticum* and *D. pigrum*) alone or in combination with DTIC, administered i.p. at 70 mg/kg (5 days/week). Mice are weighed twice weekly and euthanized at day 21 after tumor injection to count macroscopic lung metastases.

ii. Sheep model. Adult female sheep (Highlander, n=1; Scottish blackface, n=7; Scotch Mule, n=1), weighing 39-65 kg and diagnosed with naturally-occurring pre-clinical OPA, are obtained. Sheep are bedded on straw, with ad libitum access to food and water in groups of at least 2 animals and were allowed a period of adaptation of at least 24 hour before undergoing anesthesia.

Subjects are divided into control group (PBS only), and three treatment groups (infected and treated with (i) *C. pseudodiphtheriticum*, (ii) *D. pigrum*, or (iii) *C. pseudodiphtheriticum* and *D. pigrum*). Subjects are administered in an amount of 1×10^8 colony-forming units/600 μL/day, intranasally for three days, followed by a 14 day washout period. In an additional assays, a similar protocol is followed, with the addition of a chemotherapy to screen for a combination therapeutic effect.

Computed Tomography Imaging. A single-section SOMATOM Definition AS 64 slice helical CT machine (Siemens Healthcare Ltd, Camberley, UK) is used for all advanced imaging procedures.

Histopathology. OPA tissue is fixed for at least 24 h (depending on tissue thickness) in 4% formaldehyde (Genta Medical, UK) before undergoing processing using the Thermo Scientific *Excelsior* AS Tissue Processor (Thermo Scientific, UK) and embedding in paraffin. Tissue is sectioned using the Leica RM2235 rotary microtome (Leica Microsystems Ltd, UK); microtome sections of 4 μm were placed on SuperFrost Plus glass slides (Thermo Scientific, UK) and allowed to dry for a minimum of 4 h at 53° C.

For haematoxylin and eosin staining, sections are deparaffinised by 3 changes in 100% xylene for 5 min, then rehydrated by placing into alcohol; 2 changes in 100% ethanol, followed by 80% then 50% for 2 min each time. The slides are washed in running water for 2 min, before placing in haematoxylin (Shandon Harris Haematoxylin, Thermo Scientific, UK) for a maximum of 10 min. Slides are washed in running water for 2 min and then placed into Scott's tap water substitute for a maximum of 10 min until the tissue sections turned blue. Sections ae counterstained by placing them into Eosin Y (Shandon Eosin Y Cytoplasmic Counterstain, Thermo Scientific, UK) for 5 min. The slides are dehydrated by placing them into alcohol; 50% ethanol for 30 s, 80% ethanol for 30 s, then 2 changes in 100% ethanol for 2 min. The slides are placed in xylene for 10 min before being mounted with coverslips using DXP mountant (Sigma-Aldrich, UK).

Example 14: *Corynebacterium* Growth Assay

Figure 2A:
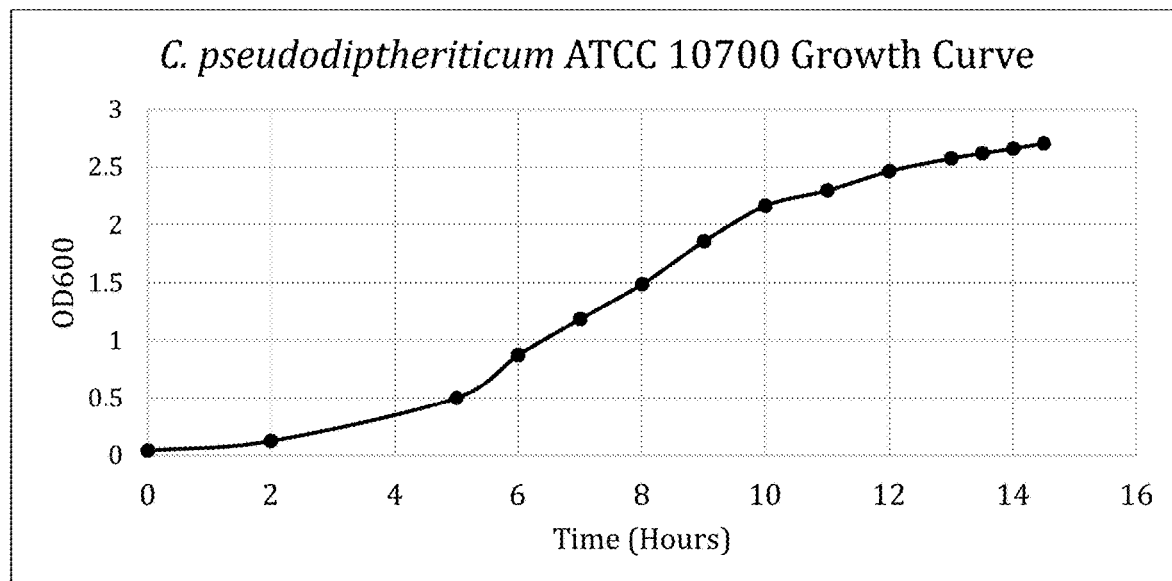
FIG. 2A, in some embodiments, illustrates a plot of OD600 measurements from growth of ATCC 10700, with OD600 for the Y axis and time in hours on the X axis.
Figure 2B:
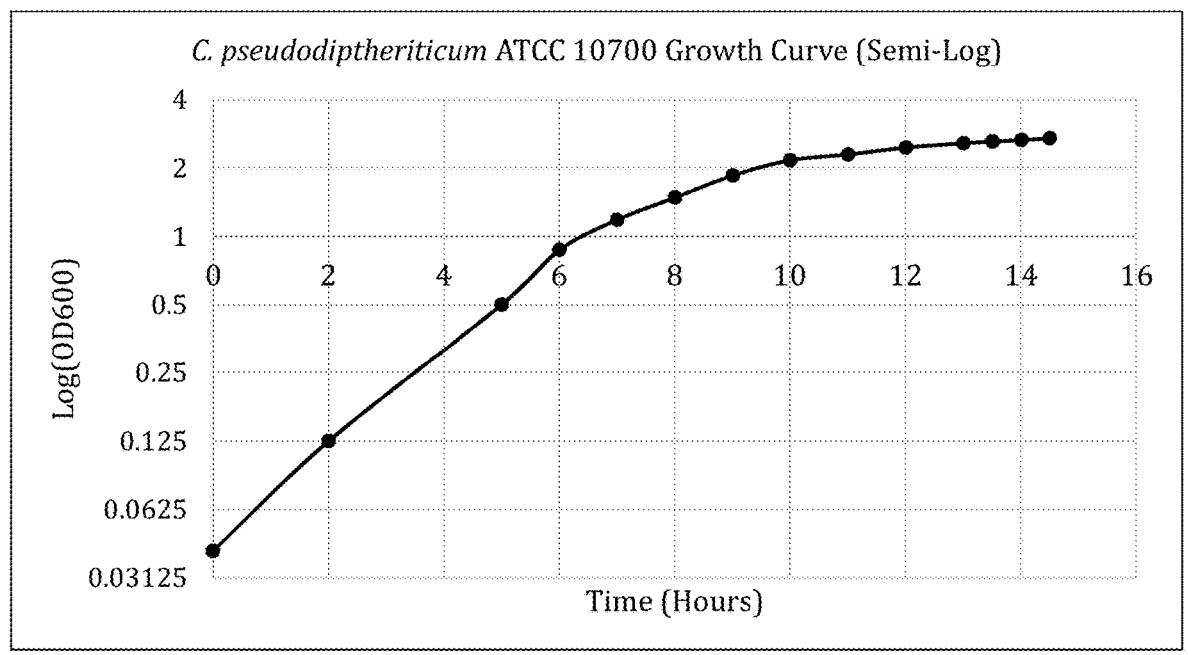
FIG. 2B, in some embodiments, illustrates a plot of OD600 measurements from growth of ATCC 10700, with Log(OD600) for the Y axis and time in hours on the X axis.
Figure 3A:
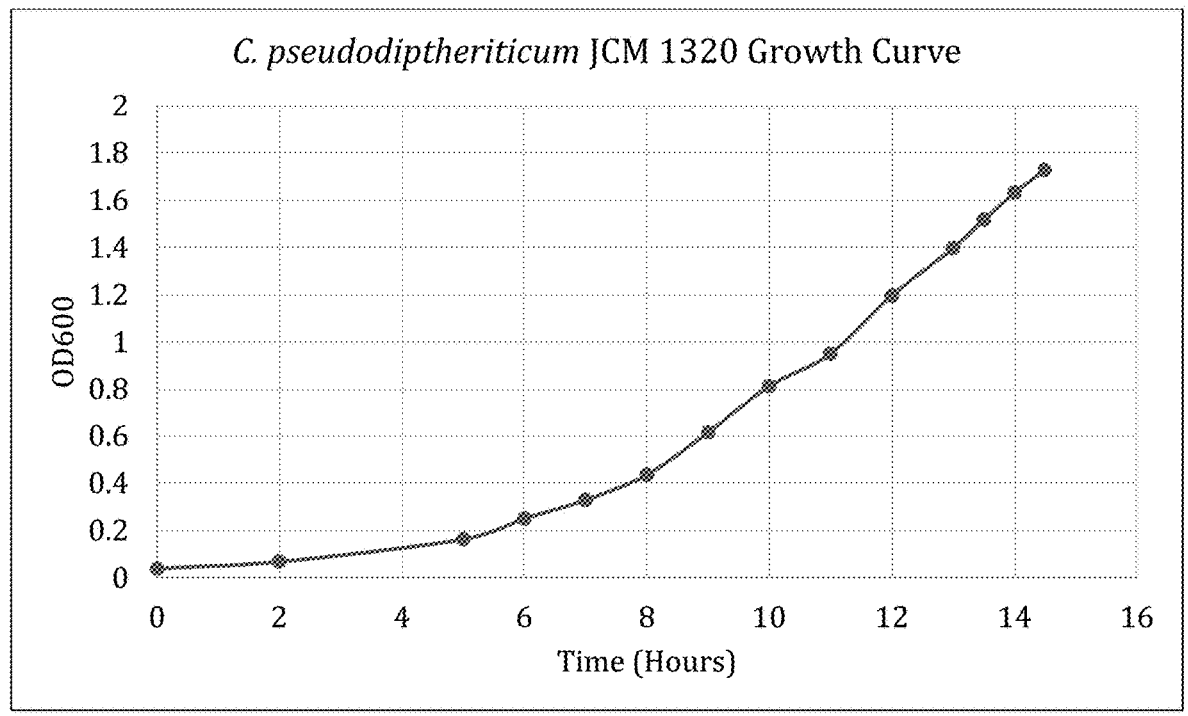
FIG. 3A, in some embodiments, illustrates a plot of OD600 measurements from growth of JCM 1320, with OD600 for the Y axis and time in hours on the X axis.
Figure 3B:
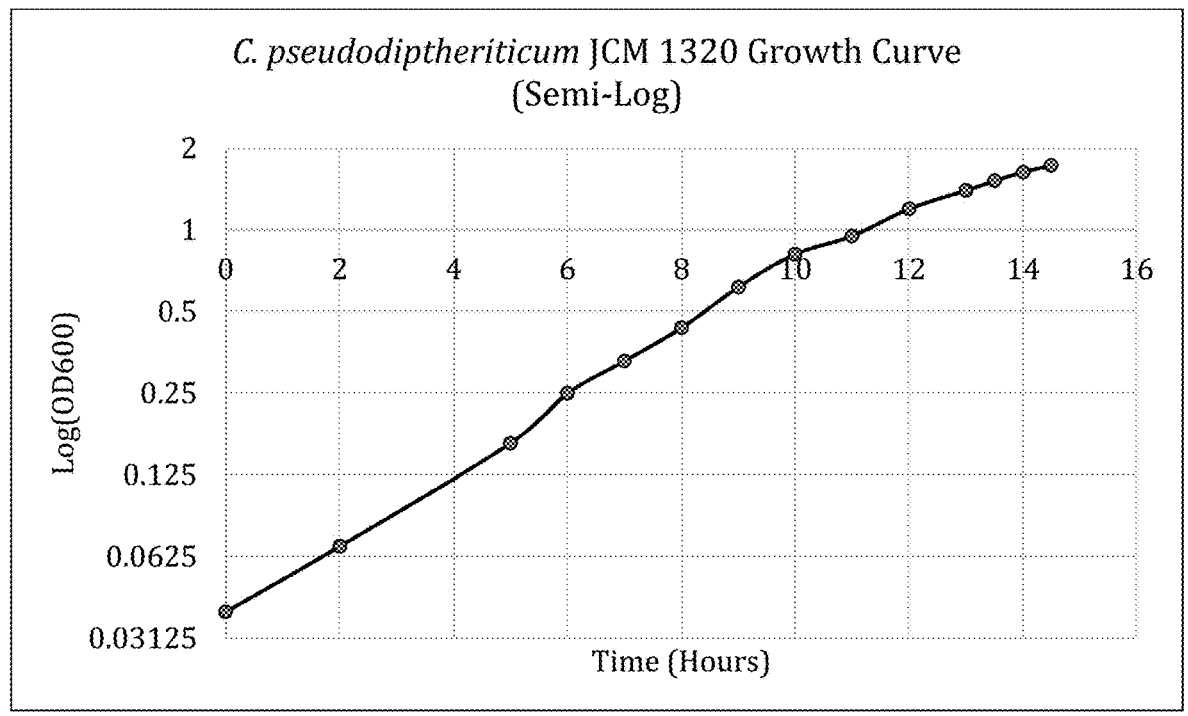
FIG. 3B, in some embodiments, illustrates a plot of OD600 measurements from growth of JCM 1320, with Log(OD600) for the Y axis and time in hours on the X axis.

The following was performed to assay growth rate attributes for *C. pseudodiptheriticum* strains. 9 mL of Columbia 1% Tween broth was inoculated with *C. pseudodiptheriticum* colonies and incubated overnight at 37 degrees Celsius, shaking at 200 rpm. From the overnight culture, an OD600 measurement was taken and 30 mL of fresh Columbia 1% Tween broth was inoculated to reach a starting OD600 of 0.04, cultures were incubated at 37 degrees Celsius shaking at 200 rpm. OD600 measurements were taken over a 14.5 hour time period. Results of OD600 measurements for growth of ATCC 10700 are show in in FIG. 2A, and shown as Log(OD600) for the Y axis in FIG. 2B. As can be seen, the doubling time during log phase (hours 2 to 6) was about 86 minutes. Results of OD600 measurements for growth of JCM 1320 are show in in FIG. 3A, and shown as Log (OD600) for the Y axis in FIG. 3B. As can be seen, the doubling time during log phase (hours 2 to 6) was about 129 minutes.

Figure 4A:
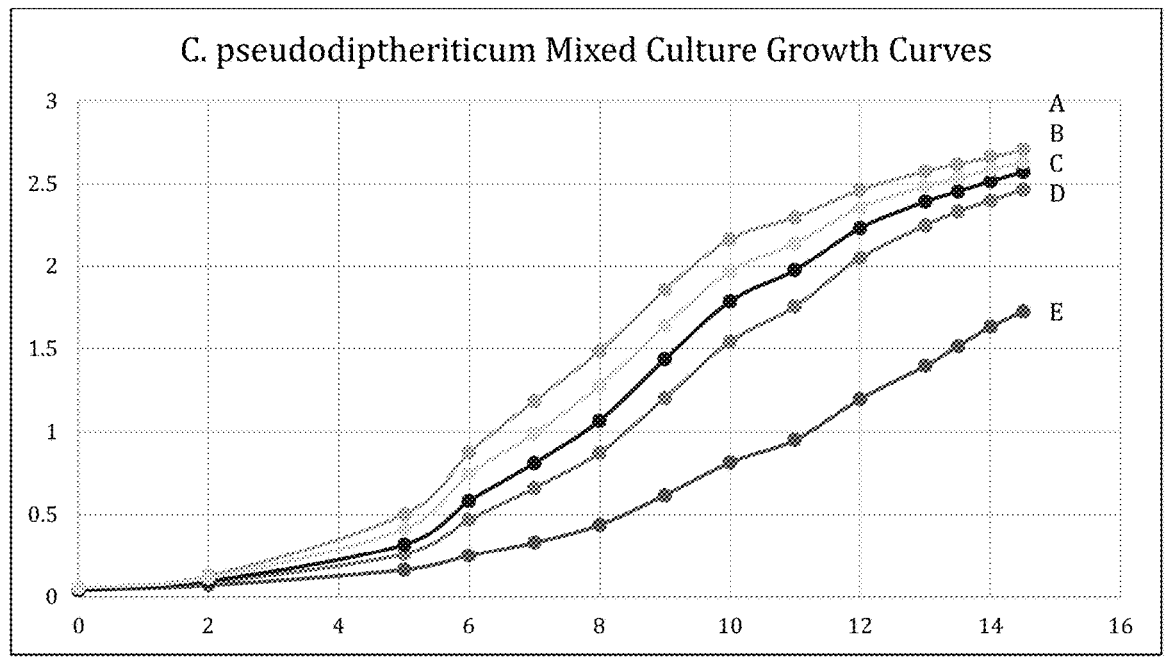
FIG. 4A, in some embodiments, illustrates a plot of OD600 measurements from growth of cultures having varying amounts of ATCC 10700 and JCM 1320, with OD600 for the Y axis and time in hours on the X axis.
Figure 4B:
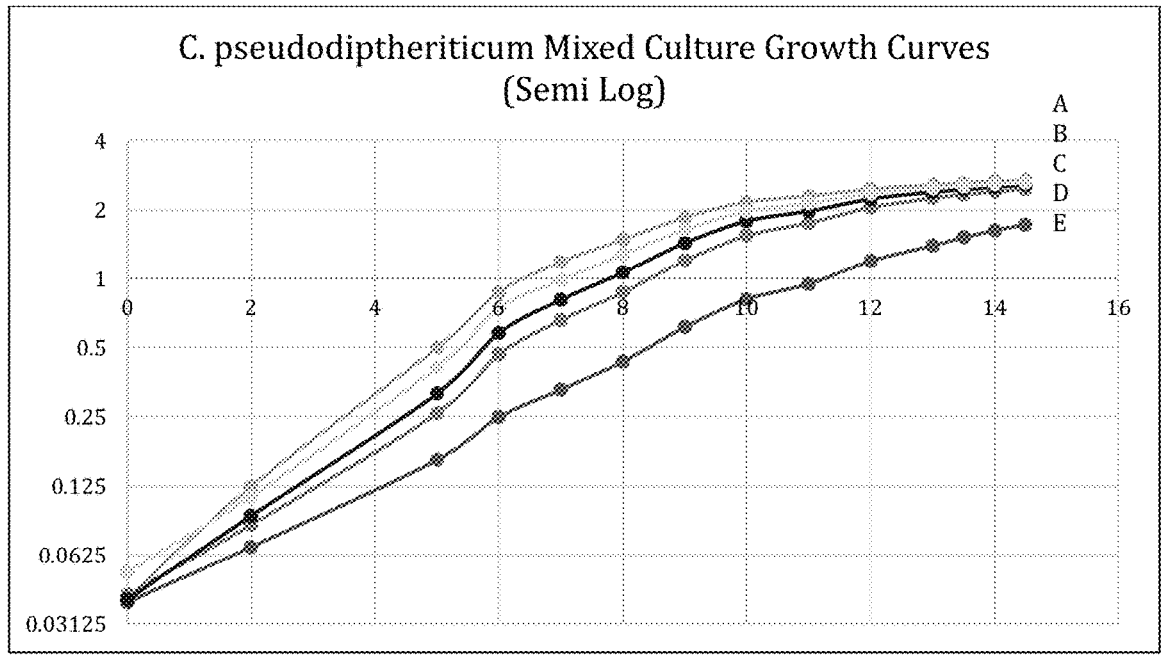
FIG. 4B, in some embodiments, illustrates a plot of OD600 measurements from growth of cultures having varying amounts of ATCC 10700 and JCM 1320, with Log (OD600) for the Y axis and time in hours on the X axis.

To assay co-culture growth, starting inoculum was varied to achieve mixed cultures while maintaining starting OD600 of 0.04. For example, diluting overnight culture to 0.04 for 400 uL for a 75% JCM 1320 25% ATCC 10700 mix, required 300 uL from the JCM 1320 culture and 100 uL from the ATCC 10700 culture. OD600 measurements were taken over a 14.5 hour time period. Results of OD600 measurements for growth are shown in in FIG. 4A, where samples A, B, C, D, and E are 100% ATCC 10700, 25% JCM 1320 and 75% ATCC 10700, 50% JCM 1320 and 50% ATCC 10700, 75% JCM 1320 and 25% ATCC 10700, and 100% JCM 1320, respectively. Results of Log(OD600) measurements for growth are shown in in FIG. 4B, with the same sample order ordering of data trendlines as in FIG. 4A. Doubling times were as follows: 100% ATCC 10700 [86 minutes], 25% JCM 1320 and 75% ATCC 10700 [89 minutes], 50% JCM 1320 and 50% ATCC 10700 [91 minutes], 75% JCM 1320 and 25% ATCC 10700 [98 minutes], and 100% JCM 1320 [129 minutes]. Doubling time appeared primarily driven by the ATCC 10700 strain. Final stationary phase cell density of mixed cultures was within similar range ($OD_{600}\pm0.1$).

Example 15: Consortia Growth Assays

Figure 5:
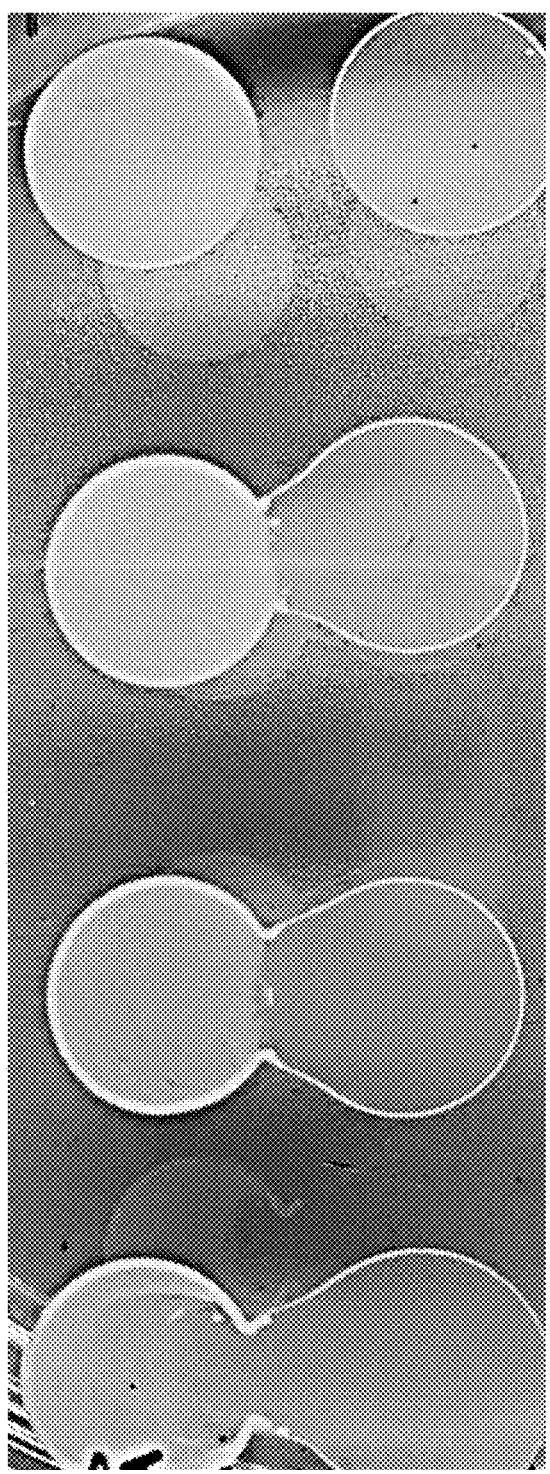
FIG. 5, in some embodiments, is an image capture of an agar plate, showing four spottings of ATCC 10700 on the left, and four spottings of JCM 1320 on the right. The image capture was taken after 24 hours of growth.

The following was performed to assay co-culture attributes for strains of *C. pseudodiptheriticum*. First, a direct co-culture of *C. pseudodiptheriticum* strains ATCC 10700 and JCM 1320 was performed. Both *C. pseudodiptheriticum* strains were spotted in close proximity at the same time on a Columbia 1% Tween agar plate: four spottings of ATCC 10700 on the left, and for spottings of JCM 1320 on the right. An image capture was taken after 24 hours from spotting, as shown in FIG. 5. As can be seen in FIG. 5, the cultures do not display features of antagonism between the different strains. This is an unexpected result, as co-culturing of *C. pseudodiptheriticum* clinical isolates has not been reported to date.

Figure 6:
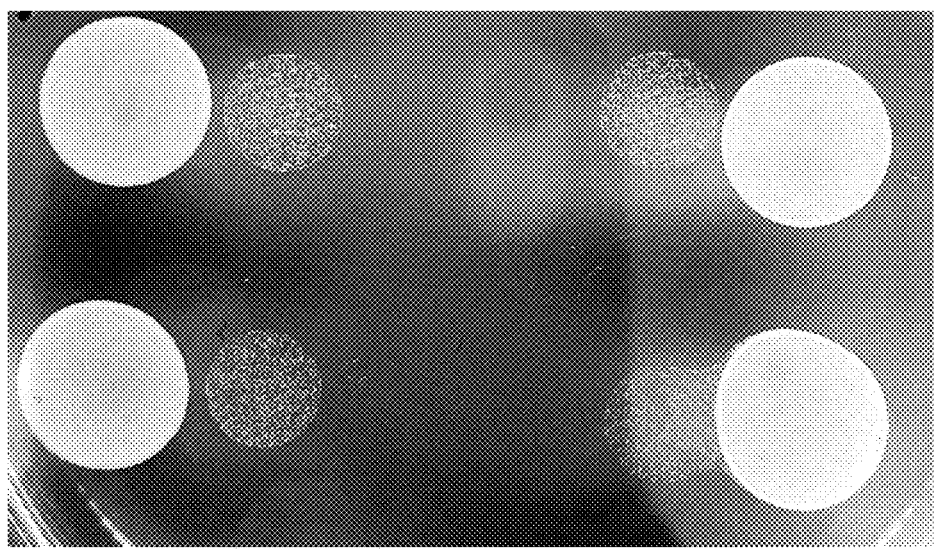
FIG. 6, in some embodiments, is an image capture of an agar plate, showing columns of left to right with two spottings of ATCC 10700, two spottings of *D. pigrum*, two spottings of *D. pigrum*, and two spottings of JCM 1320. The image capture was taken after 24 hours of growth.

Second, a direct co-culture of *C. pseudodiptheriticum* strain ATCC 10700 or JCM 1320, and *D. pigrum* was performed. An image capture was taken after 24 hours from spotting, as shown in FIG. 6. Referring to FIG. 6, on the left is a column after two spottings of ATCC 10700 and just to the right of that is a column after two spottings of *D. pigrum*. On the right of the image is a column after two spottings of *D. pigrum* and just to the right of that is a column after two spottings of JCM 1320. As can be seen in FIG. 6, the cultures do not display features of antagonism between the different strains.

While some embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition comprising:
   a live, purified population of bacteria comprising:
   at least three different strains of *Dolosigranulum pigrum,*
      wherein the at least three different strains of *Dolosigranulum pigrum* provide various bactericidal mechanisms,
      wherein the at least three different strains of *Dolosigranulum pigrum* are a lyophilized population of bacteria,
      wherein the at least three different strains of *Dolosigranulum pigrum* are present in a total amount of at least 10^3 CFU, and
      wherein two strains of the at least three different strains of *Dolosigranulum pigrum* are present individually in an amount of up to about 40% of total CFUs for CFUs present in the live, purified population of bacteria; and
   a pharmaceutically acceptable excipient.

2. The pharmaceutical composition of claim 1, wherein the pharmaceutical composition is in a nasal spray bottle.

3. The pharmaceutical composition of claim 1, wherein at least one of the at least three different strains of *Dolosigranulum pigrum* is a strain selected from the group consisting of *Dolosigranulum pigrum* deposited under accession numbers LMG P-31124 and LMG P-31154.

4. The pharmaceutical composition of claim 3, wherein the pharmaceutical composition is in a nasal spray bottle.

5. The pharmaceutical composition of claim 1, wherein the live, purified population of bacteria is present in the total amount of up to $10^{15}$ CFU.

6. The pharmaceutical composition of claim 1, wherein the live, purified population of bacteria is present in the total amount of $10^3$ to $10^{12}$ CFU.

7. The pharmaceutical composition of claim 1, wherein the live, purified population of bacteria comprises up to 10 strains.

8. The pharmaceutical composition of claim 1, wherein the various bactericidal mechanisms are directed to *S. aureus*.

9. The pharmaceutical composition of claim 1, wherein the live, purified population of bacteria comprises 4 or 5 strains.

\* \* \* \* \*